US009650628B2

(12) United States Patent
Amorese et al.

(10) Patent No.: US 9,650,628 B2
(45) Date of Patent: May 16, 2017

(54) COMPOSITIONS AND METHODS FOR TARGETED NUCLEIC ACID SEQUENCE ENRICHMENT AND HIGH EFFICIENCY LIBRARY REGENERATION

(71) Applicant: NuGEN Technologies, Inc., San Carlos, CA (US)

(72) Inventors: Doug Amorese, Los Altos, CA (US); Chris Armour, Kirkland, WA (US); Nurith Kurn, Palo Alto, CA (US)

(73) Assignee: NUGEN TECHNOLOGIES, INC., San Carlos, CA (US)

( * ) Notice: Subject to any disclaimer, the term of this patent is extended or adjusted under 35 U.S.C. 154(b) by 0 days.

(21) Appl. No.: 13/750,768

(22) Filed: Jan. 25, 2013

(65) Prior Publication Data

US 2013/0231253 A1 Sep. 5, 2013

Related U.S. Application Data

(60) Provisional application No. 61/591,241, filed on Jan. 26, 2012.

(51) Int. Cl.
*C12N 15/10* (2006.01)
*C12N 15/66* (2006.01)

(52) U.S. Cl.
CPC ..... *C12N 15/1068* (2013.01); *C12N 15/1072* (2013.01); *C12N 15/66* (2013.01)

(58) Field of Classification Search
None
See application file for complete search history.

(56) References Cited

U.S. PATENT DOCUMENTS

| | | |
|---|---|---|
| 4,362,867 A | 12/1982 | Paddock |
| 4,458,066 A | 7/1984 | Caruthers et al. |
| 4,469,863 A | 9/1984 | Ts'o et al. |
| 4,582,877 A | 4/1986 | Fairchok et al. |
| 4,876,187 A | 10/1989 | Duck et al. |
| 4,935,357 A | 6/1990 | Szybalski |
| 4,942,124 A | 7/1990 | Church |
| 4,988,617 A | 1/1991 | Landegren et al. |
| 4,996,143 A | 2/1991 | Heller et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,386,023 A | 1/1995 | Sanghvi et al. |
| 5,399,491 A | 3/1995 | Kucian et al. |
| 5,409,818 A | 4/1995 | Davey et al. |
| 5,418,149 A | 5/1995 | Gelfand et al. |
| 5,427,929 A | 6/1995 | Richards et al. |
| 5,480,784 A | 1/1996 | Kacian et al. |
| 5,494,810 A | 2/1996 | Barany et al. |
| 5,508,169 A | 4/1996 | Deugau et al. |
| 5,508,178 A | 4/1996 | Rose et al. |
| 5,510,270 A | 4/1996 | Fodor et al. |
| 5,525,471 A | 6/1996 | Zeng |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,602,240 A | 2/1997 | De Mesmaeker et al. |
| 5,637,684 A | 6/1997 | Cook et al. |
| 5,641,658 A | 6/1997 | Adams et al. |
| 5,644,048 A | 7/1997 | Yau et al. |
| 5,665,549 A | 9/1997 | Pinkel et al. |
| 5,667,976 A | 9/1997 | Van Ness et al. |
| 5,667,979 A | 9/1997 | Berrens |

(Continued)

FOREIGN PATENT DOCUMENTS

| | | |
|---|---|---|
| CA | 2444926 A1 | 11/2002 |
| EP | 0365627 B1 | 5/1990 |

(Continued)

OTHER PUBLICATIONS

Borodina et al. Methods in enzymology 500 (2011): 79-98; published on Jan. 1, 2011.*
Tucker et al. The American Journal of Human Genetics (2009) 85: 142-154.*
Rothberg et al. Nature (2011) 475: 348-352 + 25 pages of Supplementary Information.*
AB Applied Biosystems. The solid 3 system enabling the next generation of science. Presentation. 2009.
Adessi, et al., Solid phase DNA amplification: characterisation of primer attachment and amplfication mechanisms. Nucleic Acids Research. Oct. 15, 2000 28:(20): e87.
Agilent Technologies. Agilent Technologies adds human exon kit to next-generation-sequencing target enrichment portfolio. GenomicsNews.com. Posted 2009 Sep. 23, 2009. Avaialble at http://www.genomicsnews.com/index.aspx?ID=103607&sm=Agilent%20technologies%20adds%20human%20exo. Accessed Oct. 6, 2009.

(Continued)

*Primary Examiner* — Angela M Bertagna
(74) *Attorney, Agent, or Firm* — Wilson Sonsini Goodrich & Rosati

(57) ABSTRACT

The present invention provides methods, compositions and kits for targeted nucleic acid sequence enrichment in a nucleic acid sample and for high efficiency nucleic acid library generation for next generation sequencing (NGS). Specifically, the methods, compositions and kits provided herein are useful for the production and capture of amplification-ready, target-specific and strand-specific regions of interest from nucleic acid samples containing complex DNA.

37 Claims, 4 Drawing Sheets

(56) References Cited

U.S. PATENT DOCUMENTS

| | | |
|---|---|---|
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissmann et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Berg et al. |
| 6,107,023 A | 8/2000 | Reyes et al. |
| 6,110,709 A | 8/2000 | Ausubel et al. |
| 6,150,112 A | 11/2000 | Weissmann et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,190,865 B1 | 2/2001 | Jendrisak et al. |
| 6,194,211 B1 | 2/2001 | Richards et al. |
| 6,197,501 B1 | 3/2001 | Cremer et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Maceivicz |
| 6,287,766 B1 | 9/2001 | Nolan et al. |
| 6,287,825 B1 | 9/2001 | Weissmann et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Luktanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,913,884 B2 | 7/2005 | Stuelpnagel et al. |
| 6,917,726 B2 | 7/2005 | Levene et al. |
| 6,924,104 B2 | 8/2005 | Weissmann et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,056,716 B2 | 6/2006 | Potter et al. |
| 7,060,441 B2 | 6/2006 | Bourget et al. |
| 7,094,536 B2 | 8/2006 | Kurn |
| 7,115,400 B1 | 10/2006 | Adessi et al. |
| 7,170,050 B2 | 1/2007 | Turner |
| 7,175,982 B1 | 2/2007 | McCarthy et al. |
| 7,176,025 B2 | 2/2007 | Kurn et al. |
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil |
| 7,276,720 B2 | 10/2007 | Ulmer |
| 7,294,461 B2 | 11/2007 | Kurn |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,741,463 B2 * | 6/2010 | Gormley ............... C12Q 1/6855 435/91.1 |
| 7,771,934 B2 | 8/2010 | Kurn |
| 7,771,946 B2 | 8/2010 | Kurn |
| 7,803,550 B2 | 9/2010 | Makarov et al. |
| 7,846,666 B2 | 12/2010 | Kurn et al. |
| 7,846,733 B2 | 12/2010 | Kurn |
| 7,867,703 B2 | 1/2011 | Sampson et al. |
| 7,939,258 B2 | 5/2011 | Kurn et al. |
| 7,948,015 B2 | 5/2011 | Rothberg et al. |
| 7,985,565 B2 | 7/2011 | Mayer et al. |
| 8,017,335 B2 | 9/2011 | Smith |
| 8,034,568 B2 | 10/2011 | Kurn et al. |
| 8,053,192 B2 | 11/2011 | Bignell et al. |
| 8,071,311 B2 | 12/2011 | Kurn |
| 8,143,001 B2 | 3/2012 | Kurn et al. |
| 8,334,116 B2 | 12/2012 | Kurn |
| 8,465,950 B2 | 6/2013 | Kurn et al. |
| 8,492,095 B2 | 7/2013 | Kurn |
| 8,512,956 B2 | 8/2013 | Kurn et al. |
| 8,551,709 B2 | 10/2013 | Kurn et al. |
| 8,852,867 B2 | 10/2014 | Kurn et al. |
| 8,999,677 B1 | 4/2015 | Soldatov et al. |
| 9,175,325 B2 | 11/2015 | Kurn et al. |
| 9,175,336 B2 | 11/2015 | Soldatov et al. |
| 9,181,582 B2 | 11/2015 | Kurn |

(56) References Cited

U.S. PATENT DOCUMENTS

| | | |
|---|---|---|
| 9,206,418 B2 | 12/2015 | Armour |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weissmann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0215926 A1 | 11/2003 | Kurn et al. |
| 2003/0224439 A1 | 12/2003 | Lafferty et al. |
| 2003/0232348 A1* | 12/2003 | Jones et al. .......... 435/6 |
| 2004/0002371 A1 | 1/2004 | Paquine et al. |
| 2004/0005614 A1 | 1/2004 | Kurn et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1* | 6/2005 | Jones et al. .......... 435/6 |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Lapidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0068415 A1 | 3/2006 | Jones et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0286566 A1 | 12/2006 | Lapidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0141604 A1 | 6/2007 | Gormley et al. |
| 2007/0224613 A1 | 9/2007 | Strathmann |
| 2007/0231823 A1 | 10/2007 | McKernan et al. |
| 2007/0238122 A1 | 10/2007 | Allbritton et al. |
| 2008/0038727 A1 | 2/2008 | Spier |
| 2008/0087826 A1 | 4/2008 | Harris et al. |
| 2008/0103058 A1 | 5/2008 | Siddiqi |
| 2008/0160580 A1 | 7/2008 | Adessi et al. |
| 2008/0176311 A1 | 7/2008 | Kurn |
| 2008/0182300 A1 | 7/2008 | Kurn |
| 2008/0194413 A1 | 8/2008 | Albert |
| 2008/0194416 A1 | 8/2008 | Chen |
| 2008/0206764 A1 | 8/2008 | Williams et al. |
| 2008/0213770 A1 | 9/2008 | Williams et al. |
| 2008/0241831 A1 | 10/2008 | Fan et al. |
| 2008/0242560 A1 | 10/2008 | Gunderson et al. |
| 2008/0286795 A1 | 11/2008 | Kawashima et al. |
| 2009/0011959 A1* | 1/2009 | Costa et al. .......... 506/30 |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0036663 A1 | 2/2009 | Kurn |
| 2009/0061425 A1 | 3/2009 | Lo et al. |
| 2009/0061439 A1 | 3/2009 | Buzby |
| 2009/0068645 A1 | 3/2009 | Sibson |
| 2009/0068655 A1 | 3/2009 | Williams |
| 2009/0068709 A1 | 3/2009 | Kurn |
| 2009/0105081 A1 | 4/2009 | Rodesch et al. |
| 2009/0117573 A1 | 5/2009 | Fu et al. |
| 2009/0117621 A1 | 5/2009 | Boutell et al. |
| 2009/0124514 A1 | 5/2009 | Fu et al. |
| 2009/0127589 A1* | 5/2009 | Rothberg .......... C12Q 1/6874 257/253 |
| 2009/0130721 A1 | 5/2009 | Kurn et al. |
| 2009/0203085 A1 | 8/2009 | Kurn et al. |
| 2009/0203531 A1 | 8/2009 | Kurn et al. |
| 2009/0233804 A1 | 9/2009 | Kurn et al. |
| 2009/0239232 A1 | 9/2009 | Kurn et al. |
| 2009/0275486 A1 | 11/2009 | Kurn et al. |
| 2009/0280538 A1 | 11/2009 | Patel et al. |
| 2009/0298075 A1 | 12/2009 | Travers et al. |
| 2010/0015666 A1 | 1/2010 | Brenner et al. |
| 2010/0021973 A1 | 1/2010 | Makarov et al. |
| 2010/0022403 A1 | 1/2010 | Kurn et al. |
| 2010/0029511 A1 | 2/2010 | Raymond et al. |
| 2010/0105052 A1 | 4/2010 | Drmanac et al. |
| 2010/0113296 A1 | 5/2010 | Myerson |
| 2010/0129879 A1 | 5/2010 | Ach et al. |
| 2010/0137143 A1 | 6/2010 | Rothberg et al. |
| 2010/0159559 A1 | 6/2010 | Kurn et al. |
| 2010/0167954 A1 | 7/2010 | Earnshaw et al. |
| 2010/0173394 A1 | 7/2010 | Colston, Jr. et al. |
| 2010/0203597 A1 | 8/2010 | Chen et al. |
| 2010/0273219 A1 | 10/2010 | May et al. |
| 2010/0311066 A1 | 12/2010 | Kurn |
| 2010/0323348 A1 | 12/2010 | Hamady et al. |
| 2011/0015096 A1 | 1/2011 | Chiu |
| 2011/0039732 A1 | 2/2011 | Raymond et al. |
| 2011/0104785 A1* | 5/2011 | Vaidyanathan et al. ...... 435/196 |
| 2011/0105364 A1 | 5/2011 | Kurn |
| 2011/0129827 A1 | 6/2011 | Causey et al. |
| 2011/0189679 A1 | 8/2011 | Kurn et al. |
| 2011/0224105 A1* | 9/2011 | Kurn et al. .......... 506/26 |
| 2011/0288780 A1* | 11/2011 | Rabinowitz et al. .......... 702/19 |
| 2011/0294132 A1 | 12/2011 | Kurn et al. |
| 2011/0319290 A1 | 12/2011 | Raymond et al. |
| 2012/0003657 A1 | 1/2012 | Myllykangas et al. |
| 2012/0028310 A1 | 2/2012 | Kurn et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |
| 2012/0122701 A1 | 5/2012 | Ryan et al. |
| 2012/0149068 A1 | 6/2012 | Kurn et al. |
| 2012/0156728 A1 | 6/2012 | Li et al. |
| 2012/0157322 A1 | 6/2012 | Myllykangas et al. |
| 2012/0190587 A1 | 7/2012 | Kurn et al. |
| 2012/0220483 A1 | 8/2012 | Kurn et al. |
| 2012/0237943 A1 | 9/2012 | Soldatov et al. |
| 2012/0238738 A1 | 9/2012 | Hendrickson |
| 2012/0245042 A1 | 9/2012 | Brenner et al. |
| 2012/0270212 A1* | 10/2012 | Rabinowitz et al. .......... 435/6.11 |
| 2012/0283145 A1 | 11/2012 | Wang |
| 2012/0289426 A1 | 11/2012 | Roos et al. |
| 2012/0309002 A1* | 12/2012 | Link .......... 435/6.11 |
| 2013/0059178 A1 | 3/2013 | Leamon et al. |
| 2014/0038188 A1 | 2/2014 | Kurn |
| 2014/0038236 A1 | 2/2014 | Kurn et al. |
| 2014/0065692 A1 | 3/2014 | Kurn et al. |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0378345 A1 | 12/2014 | Hindson et al. |

(56) References Cited

U.S. PATENT DOCUMENTS

| | | |
|---|---|---|
| 2015/0011396 A1 | 1/2015 | Schroeder et al. |
| 2015/0017635 A1 | 1/2015 | Myllykangas et al. |
| 2015/0284769 A1 | 10/2015 | Schroeder |
| 2016/0122756 A1 | 5/2016 | Armour |
| 2016/0130576 A1 | 5/2016 | Armour |
| 2016/0153039 A1 | 6/2016 | Amorese et al. |
| 2016/0251711 A1 | 9/2016 | Amorese et al. |
| 2016/0251712 A1 | 9/2016 | Amorese et al. |
| 2016/0265042 A1 | 9/2016 | Schroeder et al. |
| 2016/0275240 A1 | 9/2016 | Huelga et al. |

FOREIGN PATENT DOCUMENTS

| | | |
|---|---|---|
| EP | 0329822 B1 | 6/1994 |
| EP | 0667393 A2 | 8/1995 |
| EP | 0667393 A3 | 11/1995 |
| EP | 1071811 B1 | 3/2002 |
| EP | 0843735 B1 | 7/2002 |
| EP | 2272976 A1 | 1/2011 |
| EP | 2322612 A1 | 5/2011 |
| EP | 2451973 A1 | 5/2012 |
| WO | WO 92/07951 A1 | 5/1992 |
| WO | WO 93/18052 A1 | 9/1993 |
| WO | WO 94/16090 A1 | 7/1994 |
| WO | WO 96/40998 A1 | 12/1996 |
| WO | WO 97/12061 A1 | 4/1997 |
| WO | WO 97/25416 A2 | 7/1997 |
| WO | WO 97/25416 A3 | 10/1997 |
| WO | WO 98/06736 A1 | 2/1998 |
| WO | WO 98/38296 A1 | 9/1998 |
| WO | WO 98/44151 A1 | 10/1998 |
| WO | WO 99/10540 A1 | 3/1999 |
| WO | WO 99/11819 A1 | 3/1999 |
| WO | WO 99/42618 A1 | 8/1999 |
| WO | WO 00/08208 A2 | 2/2000 |
| WO | WO 00/09756 A1 | 2/2000 |
| WO | WO 00/08208 A3 | 5/2000 |
| WO | WO 00/18957 A1 | 6/2000 |
| WO | WO 00/39345 A1 | 7/2000 |
| WO | WO 00/52191 A1 | 9/2000 |
| WO | WO 00/55364 A2 | 9/2000 |
| WO | WO 00/70039 A1 | 11/2000 |
| WO | WO 01/20035 A2 | 3/2001 |
| WO | WO 01/23613 A1 | 4/2001 |
| WO | WO 01/46464 A1 | 6/2001 |
| WO | WO 01/57248 A2 | 8/2001 |
| WO | WO 01/64952 A2 | 9/2001 |
| WO | WO 00/55364 A3 | 10/2001 |
| WO | WO 01/20035 A3 | 12/2001 |
| WO | WO 02/00938 A2 | 1/2002 |
| WO | WO 01/57248 A3 | 2/2002 |
| WO | WO 02/28876 A2 | 4/2002 |
| WO | WO 02/29117 A2 | 4/2002 |
| WO | WO 02/36821 A2 | 5/2002 |
| WO | WO 02/48402 A2 | 6/2002 |
| WO | WO 02/28876 A3 | 8/2002 |
| WO | WO 02/060318 A2 | 8/2002 |
| WO | WO 02/072772 A2 | 9/2002 |
| WO | WO 02/072773 A2 | 9/2002 |
| WO | WO 02/081753 A1 | 10/2002 |
| WO | WO 02/090584 A2 | 11/2002 |
| WO | WO 01/64952 A3 | 12/2002 |
| WO | WO 03/002736 A2 | 1/2003 |
| WO | WO 03/012118 A1 | 2/2003 |
| WO | WO 02/36821 A3 | 3/2003 |
| WO | WO 03/027259 A2 | 4/2003 |
| WO | WO 02/00938 A3 | 8/2003 |
| WO | WO 02/29117 A3 | 8/2003 |
| WO | WO 02/072772 A3 | 9/2003 |
| WO | WO 02/090584 A3 | 9/2003 |
| WO | WO 03/078645 A2 | 9/2003 |
| WO | WO 02/060318 A3 | 10/2003 |
| WO | WO 03/083435 A2 | 10/2003 |
| WO | WO 02/072773 A3 | 12/2003 |
| WO | WO 03/027259 A3 | 12/2003 |
| WO | WO 03/106642 A2 | 12/2003 |
| WO | WO 03/083435 A3 | 2/2004 |
| WO | WO 03/078645 A3 | 3/2004 |
| WO | WO 02/48402 A3 | 4/2004 |
| WO | WO 2004/011665 A2 | 9/2004 |
| WO | WO 2004/092418 A2 | 10/2004 |
| WO | WO 03/106642 A3 | 11/2004 |
| WO | WO 2004/011665 A3 | 7/2005 |
| WO | WO 2005/065321 A2 | 7/2005 |
| WO | WO 2006/081222 A2 | 8/2006 |
| WO | WO 2006/086668 A2 | 8/2006 |
| WO | WO 2006/081222 A3 | 2/2007 |
| WO | WO 2007/018601 A1 | 2/2007 |
| WO | WO 2007/019444 A2 | 2/2007 |
| WO | WO 2007/030759 A2 | 3/2007 |
| WO | WO 2007/052006 A1 | 5/2007 |
| WO | WO 2007/057652 A1 | 5/2007 |
| WO | WO 2007/030759 A3 | 6/2007 |
| WO | WO 2007/136717 A1 | 11/2007 |
| WO | WO 2008/005459 A2 | 1/2008 |
| WO | WO 2008/005459 A3 | 2/2008 |
| WO | WO 2008/015396 A2 | 2/2008 |
| WO | WO 2008/033442 A2 | 3/2008 |
| WO | WO 2008/115185 A2 | 9/2008 |
| WO | WO 2008/033442 A3 | 10/2008 |
| WO | WO 2008/115185 A3 | 12/2008 |
| WO | WO 2009/053039 A1 | 4/2009 |
| WO | WO 2005/065321 A3 | 5/2009 |
| WO | WO 2009/102878 A2 | 8/2009 |
| WO | WO 2009/102896 A2 | 8/2009 |
| WO | WO 2009/112844 A1 | 9/2009 |
| WO | WO 2009/117698 A2 | 9/2009 |
| WO | WO 2009/120372 A2 | 10/2009 |
| WO | WO 2009/120374 A2 | 10/2009 |
| WO | WO 2009/120374 A3 | 12/2009 |
| WO | WO 2009/120372 A3 | 1/2010 |
| WO | WO 2010/003153 A2 | 1/2010 |
| WO | WO 2010/030683 A1 | 3/2010 |
| WO | WO 2010/039991 A2 | 4/2010 |
| WO | WO 2010/063711 A1 | 6/2010 |
| WO | WO 2010/064893 A1 | 6/2010 |
| WO | WO 2010/085715 A1 | 7/2010 |
| WO | WO 2010/115154 A1 | 10/2010 |
| WO | WO 2010/129937 A2 | 11/2010 |
| WO | WO 2011/003630 A1 | 1/2011 |
| WO | WO 2011/009941 A1 | 1/2011 |
| WO | WO 2011/019964 A1 | 2/2011 |
| WO | WO 2011/032053 A1 | 3/2011 |
| WO | WO 2011/053987 A1 | 5/2011 |
| WO | WO 2011/151777 A1 | 12/2011 |
| WO | WO 2011/156529 A2 | 12/2011 |
| WO | WO 2012/013932 A1 | 2/2012 |
| WO | WO 2013/059740 A1 | 4/2013 |
| WO | WO 2013/059746 A1 | 4/2013 |
| WO | WO 2013/112923 A1 | 8/2013 |
| WO | WO 2013/177220 A1 | 11/2013 |
| WO | WO 2014/144092 A1 | 9/2014 |
| WO | WO 2014/150931 A1 | 9/2014 |
| WO | WO 2015/131107 A1 | 9/2015 |

OTHER PUBLICATIONS

Albert, et al. Direct selection of human genomic loci by microarray hybridization. Nat Methods. Nov. 2007;4(11):903-5. Epub Oct. 14, 2007.

Anisimova, et al. Isolation, characterization and molecular cloning of duplex-specific nuclease from the hepatopancreas of the kamchatka crab. *BMC Biochemistry*. May 21, 2008 9:14 doi10.1186/1471-2091-9-14.

Anwar, et al. A stem-loop-mediated reverse transcription real-time PCR for the selective detection and quantification of the replicative strand of an RNA virus. Anal Biochem. May 1, 2006;352(1):120-8. Epub Feb. 17, 2006.

Baird, et al. Rapid SNP discovery and genetic mapping using sequenced RAD markers. PLoS One. 2008;3(10):e3376.

Beier, et al. HT sequencing in biomedicine—new approaches in preparing samples. *LABORWELT*. Jan. 9, 2008.

(56) References Cited

OTHER PUBLICATIONS

Bhattacharjee, et al. Complementing next generation sequencing technologies with Agilent's SureSelect DNA capture array. Agilent. Jul. 13, 2009.

Bibikova, et al. Targeted chromosomal cleavage and mutagenesis in drophila using zinc-finger nucleases genetics. *Genetics.* Jul. 2002. 161: 1169-1175.

Blow, N. Genomics: catch me if you can. *Nature Methods*.Jul. 2009. 6:7.539-544.

Bormann, et al. Whole methylome analysis by ultra-deep sequencing using two-base encoding PLoS One. Feb. 22, 2010;5(2):e9320.

Broude. Stem-loop oligonucleotides: a robust tool for molecular biology and biotechnology. Trends Biotechnol. Jun. 2002;20(6):249-56.

Chen, et al. Real-time quantification of microRNAs by stem-loop RT-PCR. Nucleic Acids Res. Nov. 27, 2005;33(20):e179.

Craig, et al. Identification of genetic variants using bar-coded multiplexed sequencing. Nat Methods. Oct. 2008;5(10):887-93.

Croucher, et al. A simple method for directional transcriptome sequencing using Illumina technology. Nucleic Acids Res. Dec. 2009;37(22):e148.

Dressman, et al., Transforming single DNA molecules into fluorescent magnetic particles for detection and enumeration of genetic variations. Proc Natl Sci USA. Jul. 22, 2003. 100(15): 8817-8822.

Fahy, et al., Self-sustained sequence replication (3SR): an isothermal transcription-based amplication system alternative to PCR. Genome Res. 1991. 1:25-33.

Frank. Barcrawl and Bartab: software tools for the design and implementation of barcoded primers for highly multiplexed DNA sequencing. BMC Bioinformatics. Oct. 29, 2009;10:362.

Fujiwara, et al. Direct probing: covalent attachment of probe DNA to double-stranded target DNA. Nucleic Acids Res. Dec. 15, 1998;26(24):5728-33.

Fullwood, et al. Next-generation DNA sequencing of paired-end tags (PET) for transcriptome and genome analyses. *Genome Research Open Access.* 2009. Available at http://genome.cshlp.org/content/19/4/521.long. Accessed Oct. 6, 2009.

Gnirke, et al. Solution hybrid selection with ultra-long oligonucleotides for massively parallel targeted sequencing. Nature Biotechnology. Feb. 2009; 27(2):182-9.

Gu, et al. Partitioning the c. elegans genome by nucleosome modification, occupancy, and position. Online Aug. 25, 2009. http://www.springerlink.com/content/r0gw044155823242/fulltext.pdf. Accessed Oct. 6, 2009.

Hodges, et al. Hybrid selection of discrete genomic intervals on custom-designed microarrays for massively parallel sequencing. *Nat. Protoc.* 2009; 4(6): 960-974.

International search report and written opinion dated Jan. 27, 2012 for PCT Application No. US2011/039683.

International search report and written opinion dated Feb. 24, 2011 for PCT Application No. US10/55137.

International search report and written opinion dated May 10, 2012 for PCT Application No. US2012/22448.

Kaboev, et al. PCR hot start using primers with the structure of molecular beacons (hairpin-like structure). Nucleic Acids Res. Nov. 1, 2000;28(21):E94.

Kurn. Method for generation of double stranded cDNA from RNA targets useful for global amplification, sequencing or other quantification of short RNA in a sample. Mar. 21, 2010. 1-5.

Lao, et al. Real time PCR profiling of 330 human micro-RNAs. Biotechnol J. Jan. 2007;2(1):33-5.

LC Sciences. Targeted sequencing—sample enrichment service. 2009. Available at www.lcsciences.com/products/genomics/targeted_sequencing/targeted_sequencing.html . Accessed Oct. 6, 2009.

LC Sciences. Technology—Massively parallel oligonucleotide and peptide synthesis on a micrchip based on the uParaflo microfluidic technology. Available at www.lcsciences.com/support/technology/technology.html. Accessed Oct. 6, 2009.

LC Sciences. Oligonucleotide mixture. OligoMix. 2009. Available at www.lcsciences.com/products/genomics/oligomix/oligomix_detail.html. Accessed Oct. 6, 2009.

Leamon, et al., A Massively parallel Pico TiterPlate based platform for discrete picoliter-scale polymerase chaine reactions [abstract]. *Electrophoresis.* Nov. 24, 2003(21) 3769-77.

Lefrancois, et al. Efficient yeast ChIP-Seq using multiplex short-read DNA sequencing. BMC Genomics. Jan. 21, 2009;10:37.

Lennon, et al. A scalable, fully automated process for construction of sequence-ready barcoded libraries for 454. Genome Biol. 2010;11(2):R15.

Lizardi, et al., Mutation detection and single-molecule counting using isothermal rolling-circle amplification. *Nature Genetics.* 1998 Jul. 1998.19:(3):225-32.

Marchuk, et al. Construction of T-vectors, a rapid and general system for direct cloning of unmodified PCR products. Nucleic Acids Res. Mar. 11, 1991; 19(5): 1154.

Mardis, E. New strategies and emerging technologies for massively parallel sequencing: applications in medical research. Online Apr. 17, 2009. *Genome Med.* 2009: 1(4); 40. Available at www.ncbinlm.nih.gov/pmc/aricles/PMC2684661/?tool=pubmed. Accessed Oct. 22, 2009.

Margulies, et al. Genome sequencing in microfabricated high-density picolitre reactors [abstract]. *Nature.* Sep. 15, 2005; 437 (7057): 376-80. Epub Jul. 31, 2005.

Metzker, M. Sequencing technologies—the next generation. Nat Rev Genet. Jan. 2010;11(1):31-46. Epub Dec. 8, 2009.

Meyer, et al. Targeted high-throughput sequencing of tagged nucleic acid samples. Nucleic Acids Res. 2007;35(15):e97.

Mitchell, et al. Circulating microRNAS as stable blood-based markers for cancer detection. Proc Natl Acad Sci U S A. Jul. 29, 2008;105(30):10513-8. Epub Jul. 28, 2008.

Mitra, et al., In situ localized amplification and contact replication of many individual DNA moecules. Nucleic Acids Research. 1999. 27:(24); e34.

Nayak, et al. Functional architecture of T7 RNA polymerase transcription complexes. *J Mol Biol.* Aug. 10, 2007; 371(2): 490-500.

Ng, et al. Targeted capture and massively parallel sequencing of 12 human exomes. *Nature.* Sep. 10, 2009 461, 272-276. http://www.nature.com/nature/journal/v461/n7261/full/nature08250.html. Accessed Oct. 6, 2009.

Nikolaev, et al. Detection of genomic variation by selection of a 9Mb DNA region and high throughput sequencing. *PLoS ONE.* Aug. 17, 2009 4(8): e6659.

Office action dated Jan. 16, 2013 for U.S. Appl. No. 12/938,112.

Office action dated Feb. 28, 2013 for U.S. Appl. No. 13/156,294.

Parameswaran, et al. A pyrosequencing-tailored nucleotide barcode design unveils opportunities for large-scale sample multiplexing. Nucleic Acids Res. 2007;35(19):e130.

Parkhomchuk, et al. Transcriptome analysis by strand-specific sequencing of complementary DNA. Nucleic Acids Res. Oct. 2009;37(18):e123.

Pei, et al. Site-specific cleavage of duplex DNA by semisynthetic nuclease via triple-helix formation. *Pro. Natl. Acad. Sci. USA.* Dec. 1990 87: 9858-9862.

Peng, et al. Kamchatka crab duplex-specific nuclease-mediated transcriptome subtraction method for identifying long cDNAs of differentially expressed genes. *Analytical Biochemistry.* Jan. 15, 2008 372:2, 148-155. (abstract).

Prashar, et al. Analysis of differential gene expression by display of 3' end restriction fragments of cDNAs. Proc Natl Acad Sci U S A. Jan. 23, 1996;93(2):659-63.

Ranasinghe, et al. Fluorescence based strategies for genetic analysis. Chem Commun (Camb). Nov. 28, 2005;(44):5487-502. Epub Sep. 30, 2005.

Riley, et al. A novel, rapid method for the isolation of terminal sequences from yeast artificial chromosome (YAC) clones. Nucleic Acids Res. May 25, 1990;18(10):2887-90.

Roberts, R. Restriction enzymes at NEB: over 30 years of innovation, the discovery, cloning and engineering of these essential reagents. *NEB Expression.* Winter. 2008. vol. 2.4. Available at www.neb.com/nebecomm/tech_reference/restriction_enzymes/feature_article_innovation.asp. Accessed Aug. 16, 2010.

(56) References Cited

OTHER PUBLICATIONS

Roche Company. 454 life sciences, applications—sequence capture targeted region. http://www.454.com/applications/sequence-capture-targeted-region.asp. Accessed Oct. 6, 2009.

Sanders, et al. Targeting individual subunits of the FokI restriction endonuclease to specific DNA strands, *Nucleic Acids Research*. Apr. 2009. *Nucleic Acids Res.* 37:(7):2105-15.

Schmid, et al. Chic and chec: genomic mapping of chromatin proteins. *Molecular Cell.* 2004. 16, No. 1, pp. 147-157. (abstract).

Summerer, D. Enabling technologies of genomic-scale sequence enrichment for targeted high-throughput sequencing. *Genomics.* Dec. 2009;94(6):363-8. (abstract).

Summerer, et al. Microarray-based muticycle-enrichment of genomic subsets for targeted next-generation sequencing. Accepted Jun. 18, 2009. Available at www.ncbi.nlm.nih.gov/pubmed/19638418. Accessed Oct. 6, 2009.

Timblin, et al. Application for PCR technology to subtractive cDNA cloning: identification of genes expressed specifically in murine plasmacytoma cells. Nucleic Acids Res. Mar. 25, 1990;18(6):1587-93.

Tong, et al. Detection of restriction enzyme-digested target DNA by PCR amplification using a stem-loop primer: application to the detection of hypomethylated fetal DNA in maternal plasma. Clin Chem. Nov. 2007;53(11):1906-14. Epub Sep. 27, 2007.

Varkonyi-Gasic, et al. Protocol: a highly sensitive RT-PCR method for detection and quantification of microRNAs. Plant Methods. Oct. 12, 2007;3:12.

Walker, et al., Strand displacement amplification—an isothermal, in vitro DNA amplifcation technique. *Nucleic Acids Resarch*. 1991. 20(7): 1691-1696.

Westin, et al., Anchored multiplex amplification on a microelectronic chip array. *Nature Biotechnology*. Feb. 18, 2000(2):199-204.

Wikipedia. ABI solid sequencing. Http://en.wikipedia.org/wild/ABI_Solid_Sequencing. Last modified Oct. 4, 2009. Accessed Oct. 22, 2009.

Wikipedia. DNA sequencing. Available at http://en.wikipedia.org/wiki/Next-generation_sequencing. Last modified Oct. 8, 2009. Accessed Oct. 22, 2009.

Zhang, et al. Multiplex sequencing on the SOLID platform with 10, 16, or 96 barcodes. 2009 Life technologies. www3.appliedbiosystems.com/cms/groups/mcb_marketing/documents/generaldocuments/cms_065528.pdf.

Zhulidov, et al. Simple cDNA normalization using kamchatka crab duplex=specific nuclease. *Nucleic Acids Research*. Online Feb. 18, 2004. 32:3 e37.

U.S. Appl. No. 13/938,059, filed Jul. 9, 2013, Schroeder et al.

U.S. Appl. No. 13/980,987, filed Jul. 22, 2013, Kurn et al.

Brill, et al. Synthesis of oligodeoxynucleoside phosphorodithioates via thioamidites. J. Am. Chem. Soc. 1989;111:2321-2322.

Carlsson, et al. Screening for genetic mutations. Nature. 1996;380(6571):207.

Dempcy, et al. Synthesis of a thymidyl pentamer of deoxyribonucleic guanidine and binding studies with DNA homopolynucleotides. Proc Natl Acad Sci USA. 1995;92(13):6097-101.

Egholm, et al. Peptide nucleic acids (PNA) oligonucleotide analogues with an achiral peptide backbone. J. Am. Chem. Soc. 1992;114:1895-1897.

Egholm, et al. PNA hybridizes to complementary oligonucleotides obeying the Watson-Crick hydrogen-bonding rules. Nature. 1993;365(6446):566-8.

Esteller. Cancer epigenomics: DNA methylomes and histone-modification maps. Nat Rev Genet. Apr. 2007;8(4):286-98. Epub Mar. 6, 2007.

Feinberg, et al. Hypomethylation distinguishes genes of some human cancers from their normal counterparts. Nature. Jan. 6, 1983;301(5895):89-92.

Jones, et al. The epigenomics of cancer. Cell. Feb. 23, 2007;128(4):683-92.

Kiedrowski, et al. Parabolic growth of a self-replicating hexadeoxynucleotide bearing a 3'-5'-phosphoamidate linkage. Angew. Chem. Intl. Ed. English 1991;30:423-426.

Koshkin, et al. LNA (Locked Nucleic Acid): An RNA mimic forming exceedingly stable LNA:LNA duplexes. J. Am. Chem. Soc. 1998; 120:13252-3.

Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.

Laird. Principles and challenges of genomewide DNA methylation analysis. Nat Rev Genet. Mar. 2010;11(3):191-203. doi: 10.1038/nrg2732.

Letsinger, et al. Cationic oligonucletides. J. Am Chem. Soc. 1988; 110:4470-4471.

Letsinger, et al. Effects of pendant groups at phosphorus on binding properties of d-ApA analogues. Nucleic Acids Res. 1986;14(8):3487-99.

Letsinger, et al. Phosphoramidate analogs of oligonucleotides. J Org Chem. 1970;35(11):3800-3.

Mag, et al. Synthesis and selective cleavage of an oligodeoxynucleotide containing a bridged internucleotide 5'-phosphorothioate linkage. Nucleic Acids Res. 1991;19(7):1437-41.

Mardis. Next-Generation DNA Sequencing Methods. The Annual Review of Genomics and Human Genetics. 2008; 9:387-402.

Meier, et al. Peptide nuclieic acids (PNAs)—Unusual properties of nonionic oligonucleotide analogues. Chem. Int. Ed. Engl. 1992;31:1008-1010.

Meissner, et al. Reduced representation bisulfite sequencing for comparative high-resolution DNA methylation analysis. Nucleic Acids Res. Oct. 13, 2005;33(18):5868-77. Print 2005.

Ochman, et al. Genetic applications of an inverse polymerase chain reaction. Genetics. Nov. 1988;120(3):621-3.

Office action dated Sep. 5, 2013 for U.S. Appl. No. 13/156,294.

Pauwels, et al. Biological activity of new 2-5A analogues. Chemica Scripta. 1986;26:141-9.

Pierce, et al. Linear-after-the-exponential polymerase chain reaction and allied technologies. Real-time detection strategies for rapid, reliable diagnosis from single cells. Methods Mol Med. 2007;132:65-85.

Ramsahoye, et al. Non-CpG methylation is prevalent in embryonic stem cells and may be mediated by DNA methyltransferase 3a. Proc Natl Acad Sci U S A. May 9, 2000;97(10):5237-42.

Rawls, R. Optimistic about antisense. Promising clinical results and chemical strategies for further improvements delight antisense drug researchers. C & E News. Jun. 2, 1997; 35-59.

Robertson. DNA methylation and human disease. Nat Rev Genet. Aug. 2005;6(8):597-610.

Saiki, et al. Analysis of enzymatically amplified beta-globin and HLA-DQ alpha DNA with allele-specific oligonucleotide probes. Nature. Nov. 13-19, 1986;324(6093):163-6.

Sanghvi, et al. ed. Chapters 2 and 3, ASC Symposium Series 580—Carbohydrates Modifications in Antisense Research. American Chemical Society. Washington, DC. 1994.

Sanghvi, et al. ed. Chapters 6 and 7, ASC Symposium Series 580—Carbohydrates Modifications in Antisense Research. American Chemical Society. Washington, DC. 1994.

Sawai, et al. Synthesis and properties of oligoadenylic acids containing 2'-5' phosphoramide linkage. Chem. Lett. 1984; 805-808.

Soni, et al. Progress toward ultrafast DNA sequencing using solid-state nanopores. Clin Chem. Nov. 2007;53(11):1996-2001. Epub Sep. 21, 2007.

Sprinzl, et al. Enzymatic incorporation of ATP and CTP analogues into the 3' end of tRNA. Eur J Biochem. Dec. 1977;81(3):579-89.

Stemmer, et al. Single-step assembly of a gene and entire plasmid from large numbers of oligodeoxyribonucleotides. Gene. Oct. 16, 1995;164(1):49-53.

Vincent, et al. Helicase-dependent isothermal DNA amplification. EMBO Rep. Aug. 2004;5(8):795-800. Epub Jul. 9, 2004.

Vos, et al. AFLP: a new technique for DNA fingerprinting. Nucleic Acids Res. Nov. 11, 1995;23(21):4407-14.

(56) References Cited

OTHER PUBLICATIONS

Ziller, et al. Genomic distribution and inter-sample variation of non-CpG methylation across human cell types. PLoS Genet. Dec. 2011;7(12):e1002389. doi: 10.1371/journal.pgen.1002389. Epub Dec. 8, 2011.
U.S. Appl. No. 14/030,761, filed Sep. 18, 2013, Kurn et al.
Antson, et al. PCR-generated padlock probes detect single nucleotide variation in genomic DNA. Nucleic Acids Res. Jun. 15, 2000;28(12):E58.
Bashiardes, et al. Direct genomic selection. Nat Methods. Jan. 2005;2(1):63-9.
Bentley, D. R. Whole-genome re-sequencing. Curr Opin Genet Dev. Dec. 2006;16(6):545-52. Epub Oct. 18, 2006.
Borodina, et al. A strand-specific library preparation protocol for RNA sequencing. Methods Enzymol. 2011;500:79-98. doi: 10.1016/B978-0-12-385118-5.00005-0.
Dahl, et al. Multigene amplification and massively parallel sequencing for cancer mutation discovery. Proc Natl Acad Sci U S A. May 29, 2007;104(22):9387-92. Epub May 17, 2007.
Dahl, et al. Multiplex amplification enabled by selective circularization of large sets of genomic DNA fragments. Nucleic Acids Res. Apr. 28, 2005;33(8):e71.
Fredriksson, et al. Multiplex amplification of all coding sequences within 10 cancer genes by Gene-Collector. Nucleic Acids Res. 2007;35(7):e47. Epub Feb. 22, 2007.
Hodges, et al. Genome-wide in situ exon capture for selective resequencing. Nat Genet. Dec. 2007;39(12):1522-7. Epub Nov. 4, 2007.
International search report and written opinion dated Apr. 16, 2013 for PCT Application No. US2013/023278.
Krishnakumar, et al. A comprehensive assay for targeted multiplex amplification of human DNA sequences. Proc Natl Acad Sci U S A. Jul. 8, 2008;105(27):9296-301. doi: 10.1073/pnas.0803240105. Epub Jul. 2, 2008.
Levin, et al. Comprehensive comparative analysis of strand-specific RNA sequencing methods. Nat Methods. Sep. 2010;7(9):709-15. doi: 10.1038/nmeth.1491. Epub Aug. 15, 2010.
Meuzelaar, et al. MegaPlex PCR: a strategy for multiplex amplification. Nat Methods. Oct. 2007;4(10):835-7. Epub Sep. 16, 2007.
Office action dated Jun. 27, 2013 for U.S. Appl. No. 12/938,112.
Okou, et al. Microarray-based genomic selection for high-throughput resequencing. Nat Methods. Nov. 2007;4(11):907-9. Epub Oct. 14, 2007.
Olson, M. Enrichment of super-sized resequencing targets from the human genome. Nat Methods. Nov. 2007;4(11):891-2.
Porreca, et al. Multiplex amplification of large sets of human exons. Nat Methods. Nov. 2007;4(11):931-6. Epub Oct. 14, 2007.
Stephpens, et al. Automating sequence-based detection and genotyping of SNPs from diploid samples. Nat Genet. Mar. 2006;38(3):375-81. Epub Feb. 19, 2006.
Turner, et al. Methods for genomic partitioning. Annu Rev Genomics Hum Genet. 2009;10:263-84. doi: 10.1146/annurev-genom-082908-150112.
Varley, et al. Nested Patch PCR enables highly multiplexed mutation discovery in candidate genes. Genome Res. Nov. 2008;18(11):1844-50. doi: 10.1101/gr.078204.108. Epub Oct. 10, 2008.
Young, et al. A new strategy for genome assembly using short sequence reads and reduced representation libraries. Genome Res. Feb. 2010;20(2):249-56. doi: 10.1101/gr.097956.109.
Archer, et al. Selective and flexible depletion of problematic sequences from RNA-seq libraries at the cDNA stage. BMC Genomics. May 26, 2014;15:401. doi: 10.1186/1471-2164-15-401.
International search report and written opinion dated Jul. 15, 2014 for PCT Application No. US2014/028356.
International search report and written opinion dated Jul. 29, 2014 for PCT Application No. US2014/24581.
European search report and opinion dated Nov. 28, 2013 for EP Application No. 11793123.8.

Meyer, et al. Parallel tagged sequencing on the 454 platform. Nat Protoc. 2008;3(2):267-78. doi: 10.1038/nprot.2007.520.
Office action dated Oct. 9, 2013 for U.S. Appl. No. 12/938,112.
U.S. Appl. No. 13/643,056, filed Oct. 23, 2012, Armour.
U.S. Appl. No. 14/012,409, filed Aug. 28, 2013, Kurn et al.
U.S. Appl. No. 14/211,261, filed Mar. 14, 2014, Amorese et al.
Adamczyk, et al. Synthesis of a Chemiluminescent Acridinium Hydroxylamine (AHA) for the Direct Detection of Abasic Sites in DNA. Org. Lett. 1999; 1(5):779-781.
Adamczyk, et al. O-(Fluoresceinylmethyl) hydroxylamine (OFMHA): A Fluorescent Regent for Detection of Damaged Nucleic Acids. Bioorg. & Med. Chem. Lett. 1998; 8:3599-3602.
Arraystar, Inc. Arraystar Directional RNA-seq Prep Kit (dUTP Based). CAT#: A1208. Apr. 8, 2013.
Ausubel, et al., Eds. Current Protocols in Molecular Biology. John Wiley & Sons, Inc. 1987 and updates.
Ballestar, et al. Methyl-CpG-binding proteins. Targeting specific gene repression. Eur J Biochem 2001; 268:1-6.
Bangs Laboratories, Inc. TechNote 205 retreived at: http:www.bangslab.com/technotes/205.pdf . Visited on Jul. 16, 2003. (8 pages).
Beaucage, et al. The functionalization of oligonucleotides via phosphoramidite derivative. Tetrahedron. 1993;49(10):1925-63.
Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.
Bioo Scientific. Illumina RNA-Seq Library Prep. Available at http://www.biooscientific.com/ProductsServices/NextGenSequencing/Illumina-Compatible/RNA-Seq.aspx. Accessed Jun. 16, 2014.
Bioo Scientific. NEXTflex RNA-Seq Kit. Available at http://www.biooscientific.com/ProductsServices/NextGenSequencing/Illumina-Compatible/RNA-Seq/NEXTflex%E2%84%A2RNA-SeqKit.aspx. Accessed Jun. 16, 2014.
Borodina, et al. A strand-specific library preparation protocol for RNA sequencing. Chpater 5. Methods in Enzymology. Sep. 20, 2011; 500:79-98.
Boturyn, et al. A simple and Sensitive Method for in Vitro Quantitation of Abasic Sites in DNA. Chem. Res. Toxicol. 1999; 12:476-482.
Boturyn, et al. Synthesis of Fluorescent Probes for the Detection of Abasic Sites in DNA. Tetrahedron. 1997; 53(15):5485-5492.
Brown, T.A. Ed. Molecular Biology, LabFax. Bios Scientific Publishers. Academic Press. 1991; pp. 147-148.
Buchman, et al. Selective RNA amplification: a novel method using dUMP-containing primers and uracil DNA glycosylase. PCR Methods Appl. Aug. 1993;3(1):28-31.
Burrows, et al. Oxidative Nucleobase Modifications Leading to Strand Scission. Chem Rev. May 7, 1998;98(3):1109-1151.
Carey, et al. Human Apurinic/Apyrimidinic Endonuclease in Processive. Biochem. 1999; 38:16553-16560.
Chan, et al. The biophysics of DNA hybridization with immobilized oligonucleotide probes. Biophys J. Dec. 1995;69(6):2243-55.
Clontech Laboratories, Inc. In-Fusion SMARTer Directional cDNA Library Construction Kit User Manual. Cat. No. 634933. Copyright 2013.
Cofactor genomics. Directional RNA Sequencing. Abailable at http://cofactorgenomics.com/directional-rna-sequencing. Accessed Jun. 4, 2014.
Combined search and examination report dated Apr. 24, 2013 for GB1305340.
Derisi, et al. Use of cDNA microarray to analyse gene expression patterns in human cancer. Nature Genetics. 1996; 14:457-460.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.
Erlanger, et al. Antibodies Specific for Ribonucleosides and Ribonucleotides and Their Reaction With DNA. Proc Natl Acad Sci USA. 1964; 52:68-74.
European office action dated Apr. 1, 2011 for Application No. 03771533.1.
European search report and search opinion dated Apr. 3, 2013 for Application No. 10808789.1.

(56) References Cited

OTHER PUBLICATIONS

European search report dated Oct. 18, 2007 for Application No. 3771533.1.
European search report dated Feb. 12, 2010 for Application No. 7810169.8.
European search report dated Mar. 29, 2010 for Application No. 4815722.6.
Fodor, et al. Light-Directed, spatially addressable parallel chemical synthesis. 1991; 251: 767-773.
Franca, et al. Optimizing a qPCR gene expression quantification assay for S.epidermidis biofilms: a comparison between commercial kits and a customized protocol. PLoS One. 2012;7(5):e37480. doi: 10.1371/journal.pone.0037480. Epub May 21, 2012.
Freeman, et al. Fundamentals of DNA Hybridization Arrays for Gene Expression Analysis. BioTechniques. Nov. 2000; 29:1042-1044, 1046, 1048-1055.
Freshney, R.I. ed. (1987). *Animal Cell Culture.* IRL Press: Oxford, pp. vii-xii (Table of Contents Only.).
Gait, M.J., Ed. 1984 . Oligonucleotide Synthesis: A Practical Approach. IRL Press: Oxford, pp. vii-xii (Table of Contents).
Gertz, et al. Transposase mediated construction of RNA-seq libraries. Genome Res. Jan. 2012;22(1):134-41. doi: 10.1101/gr.127373. 111. Epub Nov. 29, 2011.
Ghosh, S.S. Synthesis of 5'-Oligonucleotide Hydrazide Derivatives and Their Use in Preparation of Enzyme-Nucleic Acid Hybridization Probes. Anal. Biochem. 1989; 178:43-51.
Haraguchi, et al. Synthesis and characterization of oligodeoxynucleotides containing formamidopyrimidine lesions and nonhydrolyzable analogues. J Am Chem Soc. Apr. 3, 2002;124(13):3263-9.
Heimgartner, et al.Polyacrylic Polyhydrazides as Reagents for Detection of Glycoproteins. Anal. Biochem. 1989; 181:182-189.
Hollis, et al. Structural studies of human alkyladenine glycosylase and *E. coli* 3-methyladenine glycosylase.Mutat Res. 2000; 460(3-4):201-10.
Horn, et al. Solid supported hydrolysis of apurinic sites in synthetic oligonucleotides for rapid and efficient purification on reverse-phase cartridges. Nucl. Acids Res. 1988; 16:11559-11571.
Hottiger, et al. Strand displacement activity of the human immunodeficiency virus type 1 reverse transcriptase heterodimer and its individual subunits. J Biol Chem. Jan. 14, 1994;269(2):986-91.
Huber, et al. Processing of the primer for plus strand DNA synthesis by human immunodeficiency virus 1 reverse transcriptase. J Biol Chem. Jun. 25, 1990;265(18):10565-73.
Ide, et al. Synthesis and Damage Specificity of a Novel Probe for the Detection of Abasic Sites in DNA. Biochem. 1993; 32:8276-8283.
illumina Inc. Directional mRNA-Seq Sample Preparation—Application to prepare directional (strand specific) sample from mRNA. Oct. 2010.
International Preliminary Examination Report mailed on Mar. 22, 2006 for PCT Patent Application No. PCT/US03/15825 filed May 19, 2003, 9pages.
International search report and written opinion dated Feb. 12, 2013 for PCT/US2012/061218.
International search report and written opinion dated Oct. 18, 2013 for PCT Application No. US2013/032606.
International search report and written opinion dated Dec. 3, 2010 for PCT Application No. US10-45384.
International search report dated Jan. 2, 2008 for PCT Application No. US2007/15409.
International search report dated Jun. 14, 2005 for PCT Application No. US 2003/015825.
International search report dated Jul. 9, 2008 for PCT Application No. US2004/043710.
Jenkins, et al. The biosynthesis of carbocyclic nucleosides. Chem. Soc. Rev. 1995;169-176.
Karata, et al. Construction of a circular single-stranded DNA template containing a defined lesion. DNA Repair (Amst). Jul. 4, 2009;8(7):852-6.

Kawarada, et al. Antibodies Specific for Methylated DNA Elicited in Rabbits Recognize only a Single Strand Region of DNA Containing 7-Methylguanine. Tohuku. J Exp Med. 1986; 149:151-161.
Khrapko, et al. A method for DNA sequencing by hybridization with oligonucleotide matrix. DNA Sequence—J. DNA Sequencing and Mapping. 1991; 1:375-388.
Kim, et al. Evidence for thiol-dependent production of oxygen radicals by 4-methyl-5-pyrazinyl-3H-1,2-dithiole-3-thione (oltipraz) and 3H-1,2-dithiole-3-thione: possible relevance to the anticarcinogenic properties of 1,2-dithiole-3-thiones. Chem Res Toxicol. Mar. 1997;10(3):296-301.
Kow, et al. Detection of Abasic Sites and Oxidative DNA Base Damage Using an ELISA-like Assay. Methods. 2000; 22:164-169.
Kubo, et al. A Novel Sensitive, and Specific Assay for Abasic Sites, the Most Commonly Produced DNA Lesion. Biochem. 1992; 31:3703-3708.
Kumar, et al. A High-Throughput Method for Illumina RNA-Seq Library Preparation. Front Plant Sci. Aug. 28, 2012;3:202. doi: 10.3389/fpls.2012.00202.eCollection 2012.
Lhomme, et al. Abasic DNA Structure reactivity and recognition. Biopolymers. 1999; 52(2): 65-83.
Lindahl, T. An N-Glycosidase from *Escherichia coli* That Releases Free Uracil from DNA Containing Deaminated Cytosine Residues. Proc Natl. Acad. Sci. USA 1974; 71(9):3649-3653.
Lockhart, et al. Expression monitoring by hybridization to high-density oligonucleotide arrays. Nature Biotechnology. 1996; 14:1675-1680.
Makrigiogos, G. Fluorescent Labeling of Abasic Sites: A Novel Methodology to Detect Closely-Spaced Damage Sites in DNA. Int. J. Radiat. Biol. 1998: 74(1):99-109.
Maskos, et al. Oligonucleotide hybridisations on glass supports: a novel linker for oligonucleotide synthesis and hybridization properties of oligonucleotides synthesised in Situ. Nucl. Acids. Res. 20(7):1679-1684.
Maulik, et al. Novel Non-isotopic Detection of MutY Enzyme-recognized in DNA Via Ultrasensitive Detection of Aldehydes. Nucl. Acids. Res. 1999: 27(5):1316-1322.
McCarthy, et al. Inducible repair of O-alkylated DNA pyrimidines in *Escherichia coli*. EMBO J. 1984; 3(3):545-50.
McHugh, et al. Novel Regents for Chemical Cleavage at Abasic Sites and UV Photoproducts in DNA. Nucl. Acids. Res. 23(10): 1664-1670.
Mitra, et al. Oxidative DNA cleavage by the antitumor antibiotic leinamycin and simple 1,2-dithiolan-3-one 1-oxides: Evidence for thiol-dependent conversion of molecular oxygen to DNA-cleaving oxygen radicals mediated by polysulfides. Journal of the American Chemical Society. 1997; vol. 119(48):11691-11692.
Mizugaki, et al. Preparation of a monoclonal antibody specific for 5-methyl-2'deoxycytidine and its application for the detection of DNA methylation levels in human peripheral blood cells. Biol Pharm Bull. 1996; 19(12):1537-1540.
Molecular Probe Handbook Section 3.2 obtained from website at: http://www.probes.com/handbook/print/0302.html (Copyright © 1996-2003 by Molecular Probes, Inc.) Visited on Aug. 13, 2003. (18 pages).
Mullis, K.B et al., Eds. (1994). PCR: Polymerase Chain Reaction. Birkhauser: Boston, pp. xv-xvii (Table of Contents).
Nakamura, et al. Highly Sensitive Apurinic/Apyrimidinic site Assay Can Detect Spontaneous and Chemically Induced Depurination Under Physiological Conditions. Cancer Res. 1998; 58:222-225.
Nedderman, et al. Cloning and expression of human G/T mismatch-specific thymine-DNA glycosylase. J Biol Chem. 1996; 271(22):12767-74.
New England BioLabs Inc. NEBNext® Ultra™ Directional RNA Library Prep Kit for Illumina®. Available at https://www.neb.com/products/e7420-nebnext-ultra-directional-rna-library-prep-kit-for-illumina. Accessed Jun. 4, 2014.
Neylon, et al. Chemical and biochemical strategies for the randomization of protein encoding DNA sequences: library construction methods for directed evolution. Nucleic Acids Res. Feb. 27, 2004;32(4):1448-59. Print 2004.
Nugen, Inc. Ovation Biotin RNA Amplification and Labeling System User Guite. Catalog #2300-12. Published 2004.

(56) References Cited

OTHER PUBLICATIONS

Nugen, Inc. Technical Report #1. The Ovation Biotin System Validation for Use with Affymetrix GeneChip Arrays. Published 2004.
O'Shannessy, et al. Immobilization of Glycoconjugates by Their Oligosaccharides: Use of Hydrazido-Derivatized Matrices. Anal. Biochem. 1990; 191:1-8.
Office action dated Feb. 8, 2012 for EP Application No. 07810169.8.
Office action dated Feb. 17, 2011 for U.S. Appl. No. 12/305,633.
Office action dated Mar. 1, 2010 for U.S. Appl. No. 10/441,663.
Office action dated Mar. 7, 2007 for U.S. Appl. No. 10/441,663.
Office action dated May 16, 2011 for U.S. Appl. No. 11/948,784.
Office action dated May 25, 2006 for U.S. Appl. No. 10/441,663.
Office action dated Jun. 6, 2012 for U.S. Appl. No. 10/441,663.
Office action dated Jun. 19, 2013 for U.S. Appl. No. 12/855,611.
Office action dated Jun. 30, 2008 for U.S. Appl. No. 11/026,280.
Office action dated Jul. 5, 2007 for U.S. Appl. No. 10/441,663.
Office action dated Jul. 8, 2009 for U.S. Appl. No. 10/441,663.
Office action dated Jul. 13, 2007 for U.S. Appl. No. 11/026,280.
Office action dated Jul. 15, 2008 for U.S. Appl. No. 10/441,663.
Office action dated Aug. 18, 2010 for U.S. Appl. No. 12/305,633.
Office action dated Sep. 9, 2010 for U.S. Appl. No. 10/441,663.
Office action dated Sep. 18, 2006 for U.S. Appl. No. 10/441,663.
Office action dated Sep. 24, 2009 for U.S. Appl. No. 10/441,663.
Office action dated Oct. 14, 2010 for U.S. Appl. No. 11/948,784.
Office action dated Nov. 7, 2012 for U.S. Appl. No. 13/411,170.
Office action dated Nov. 13, 2012 for U.S. Appl. No. 12/855,611.
Office action dated Dec. 5, 2008 for U.S. Appl. No. 10/441,663.
Office action dated Dec. 17, 2007 for U.S. Appl. No. 10/441,663.
Openwetware. Directional-RNAseq Prep. Available at http://openwetware.org/wiki/Directional-RNAseq_Prep. Accessed Jun. 4, 2014.
Pang, et al. Use of modified nucleotides and uracil-DNA glycosylase (UNG) for the control of contamination in the PCR-based amplification of RNA. Molecular and Cellular Probes. 1992; 6:251-256.
Pease, et al. A rapid, directional RNA-seq library preparation workflow for Illumina [reg] sequencing. Nature Methods. 2012; 9, No. 3.
Pease, et al. Light-generated oligonucleotide arrays for rapid DNA sequence analysis. Proc. Natl. Acad. Sci. USA 1994; 91:5022-5026.
Pease, et al. Rapid, directional RNA-seq library preparation kits for formalin-fixed paraffin-embedded RNA. Nature Methods. 2012; 9: Published online Sep. 27, 2012.
Pollack, et al. Genome-wide analysis of DNA copy-number changes using cDNA microarrays. Nature Genet. 1999; 23:41-46.
Proudnikov, et al. Chemical methods of DNA and RNA fluorescent labeling. Nucleic Acids Res. Nov. 15, 1996;24(22):4535-42.
Sambrook, J. et al., Eds. (1989). *Molecular Cloning: A Laboratory Manual*. 2nd Edition, Cold Spring Harbor Laboratory Press, pp. xi-xxxviii (Table of Contents).
Sano, et al. Detection of heavy methylation in human repetitive DNA subsets by a monoclonal antibody against 5-methylcytosine. Biochim Biophys Acta. 1988; 951(1):157-65.
Sartori, et al. A novel uracil-DNA glycosylase with broad substrate specificity and an unusual active site. EMBO J. 2002; 21(12):3182-91.
Schena, et al. Parallel human genome analysis: microarray-based espression monitoring of 1000 genes. Proc Natl. Acad. Sci. USA Biochemistry. 1996; 93:10614-10619.
Schena, et al. Quantitative monitoring of gene expression patterns with a complementary DNA microarray. Science. 1995; 270:467-470.
Shalon, et al. Parallel human genome analysis: microarray system for analyzing complex DNA samples using two-color fluorescent probe hybridization. Genome Res. 1996; 6:639-645.
Shida, et al. Cleavage of Single-and double-Stranded DNAs Containing an Abasic Residue by *Escherichia coli* Exonuclease III (AP Endonuclease VI) Nucl. Acids. Res. 1996; 24(22):4572-4576.
Slupphaug, et al. Low incorporation of dUMP by some thermostable DNA polymerases may limit their use in PCR amplifications. Anal. Biochem. 1993; 211:164-169.
Sohail, et al. Human activation-induced cytidine deaminase causes transcription-dependent, strand-biased C to U deaminations. Nucleic Acids Res. 2003; 31(12):2990-4.
Srivastava, et al. Mammalian Abasic Site Base Excision Repair. Identification of the Reaction Sequence and Rate-Determining Steps. J. Biol. Chem. 1998; 273(22):21203-21209.
Steullet, et al. Clevage of Abasic Sites in DNA by Intercalator-amines. Bioorganic and Medicinal Chem. 1999; 7:2531-2540.
Stratagene catalog, Gene Characterizatin Kits. 1988 p. 39.
Sugiyama, et al. Chemistry of thermal degradation of abasic sites in DNA. Mechanistic investigation on thermal DNA stand clevage of alkylated DNA. Chem. Res. Toxicol. 1994; 1:673-683.
Vairapandi, et al. Partial purification and characterization of human 5-methylcytosine-DNA glycosylase. Oncogene. 1996; 13(5):933-8.
Vairapandi, et al. Human DNA-demethylating activity: a glycosylase associated with RNA and PCNA. J Cell Biochem. 2000; 79(2):249-60.
Westburg. Fast, Directional RNA-Seq Library Prep. Abailable at http://www.westburg.eu/lp/rna-seq-library-preparation. Accessed on Jun. 4, 2014.
Wilchek, et al. Labeling Glycoconjugates with Hydrazide Reagents. Methods Enzymol. 1987; 138:429-442.
Wolffe, et al. DNA demethylation. Proc Natl Acad Sci USA. 1999; 96(11):5894-6.
Zalipsky, S. Functionalized Poly(ethylene glycol) for Preparation of Biologically Relevant Congugates. Bioconjugate Chem. 1995; 6:150-165.
Zang, et al. DNA alkylation by leinamycin can be triggered by cyanide and phosphines. Bioorg Med Chem Lett. Jun. 18, 2001;11(12):1511-5.
Zhu, et al. Overexpression of 5-methylcytosine DNA glycosylase in human embryonic kidney cells EcR293 demethylates the promoter of a hormone-regulated reporter gene. Proc Natl Acad Sci USA. 2001; 98(9):5031-6.
Zhu, et al. 5-Methylcytosine DNA glycosylase activity is also present in the human MBD4 (G/T mismatch glycosylase) and in a related avian sequence. Nucleic Acids Res. 2000; 28(21):4157-65.
U.S. Appl. No. 14/634,326, filed Feb. 27, 2015, Schroeder.
Ahmed. Sequencing of Low-Diversity Libraries. Feb. 28, 2012. http://cofactorgenomics.com/sequencing-low-diversity-libraries/.
Diagnosing problems with phasing and pre-phasing on Illumina platforms. Loman Labs. Nov. 21, 2013. http://nickloman.github.io/high-throughput%20sequencing/2013/11/21/diagnosing-problems-with-phasing-and-pre-phasing-on-illumina-platforms/.
Fadrosh, et al. An improved dual-indexing approach for multiplexed 16S rRNA gene sequencing on the Illumina MiSeq platform. Microbiome. Feb. 24, 2014;2(1):6. doi: 10.1186/2049-2618-2-6.
Faircloth, et al. Not all sequence tags are created equal: designing and validating sequence identification tags robust to indels. PLoS One. 2012;7(8):e42543. doi: 10.1371/journal.pone.0042543. Epub Aug. 10, 2012.
Gu, et al. Preparation of reduced representation bisulfite sequencing libraries for genome-scale DNA methylation profiling. Nat Protoc. Apr. 2011;6(4):468-81. doi: 10.1038/nprot.2010.190. Epub Mar. 18, 2011.
Kozich, et al. Development of a dual-index sequencing strategy and curation pipeline for analyzing amplicon sequence data on the MiSeq Illumina sequencing platform. Appl Environ Microbiol. Sep. 2013;79(17):5112-20. doi: 10.1128/AEM.01043-13. Epub Jun. 21, 2013.
Krueger, et al. Large scale loss of data in low-diversity illumina sequencing libraries can be recovered by deferred cluster calling. PLoS One. Jan. 28, 2011;6(1):e16607. doi: 10.1371/journal.pone.0016607.
Krueger. Loss of data in low-diversity libraries can be recovered by deferred cluster calling. Poster Jan. 29, 2011. http://seqanswers.com/forums/showthread.php?t=9150.

(56) References Cited

OTHER PUBLICATIONS

Leonard. What is a reliable method for multiplexing more than 384 samples on a MiSeq run? Posted Aug. 19, 2013. http://www.researchgate.net/post/What_is_a_reliable_method_for_multiplexing_more_than_384_samples_on_a_MiSeq_run2.
Office action dated Mar. 9, 2015 for CN Application No. 201380006942.4.
Nextera® Rapid Capture Enrichment Low-Plex Pooling Guidelines. Technical Note: DNA Analysis. 2014. http://www.illumina.com/content/dam/illumina-marketing/documents/products/technotes/technote-nextera-rapid-capture-low-plex-pooling-guidelines.pdf.
SEQanswers. MiSeq cluster generation problems. Posted Mar. 17, 2012. http://seqanswers.com/forums/showthread.php?t=18499.
SEQanswers. Sequencing a Low diversity library on the HiSeq. Posted Nov. 18, 2011. http://seqanswers.com/forums/showthread.php?t=18499.
Singapore written opinion dated Mar. 17, 2015 for SG Application No. 11201401628W.
Wu, et al. Phasing Amplicon Sequencing for Robust Microbial Community Analysis. I-2630. 2014. http://www.asmonlineeducation.com/php/asm2014abstracts/data/papers/I-2630.htm.
Alvarado, et al. Multiplexed direct genomic selection (MDiGS): a pooled BAC capture approach for highly accurate CNV and SNP/INDEL detection. Nucleic Acids Res. Jun. 2014;42(10):e82. doi: 10.1093/nar/gku218. Epub Mar. 20, 2014.
CNV detection by ion semiconductor sequencing. Life Technologies. 2014.
McClure, et al. Bovine exome sequence analysis and targeted SNP genotyping of recessive fertility defects BH1, HH2, and HH3 reveal a putative causative mutation in SMC2 for HH3. PLoS One. Mar. 25, 2014;9(3):e92769. doi: 10.1371/journal.pone.0092769. eCollection 2014.
Pabinger, et al. A survey of tools for variant analysis of next-generation genome sequencing data. Brief Bioinform. Mar. 2014;15(2):256-78. doi: 10.1093/bib/bbs086. Epub Jan. 21, 2013.
Xiao, et al. Sequential amplification of flanking sequences by Y-shaped adaptor dependent extension using multiple templates. Zhi Wu Sheng Li Yu Fen Zi Sheng Wu Xue Xue Bao (Journal of Plant Physiology and Molecular Biology). Feb. 2007;33(1):85-90.
Zheng, et al. Titration-free 454 sequencing using Y adapters. Nat Protoc. Aug. 18, 2011;6(9):1367-76. doi: 10.1038/nprot.2011.369.
Bower, et al. Targeted rapid amplification of cDNA ends (T-RACE)—an improved RACE reaction through degradation of non-target sequences. Nucleic Acids Res. Nov. 2010;38(21):e194. doi: 10.1093/nar/gkq816. Epub Sep. 15, 2010.
Chen, et al. BisQC: an operational pipeline for multiplexed bisulfite sequencing. BMC Genomics. Apr. 16, 2014;15:290. doi: 10.1186/1471-2164-15-290.
Chenchik, et al. Full-length cDNA cloning and determination of mRNA 5' and 3' ends by amplification of adaptor-ligated cDNA. Biotechniques. Sep. 1996;21(3):526-34.
European search report and opinion dated May 22, 2015 for EP Application No. 12842163.3.
International search report and written opinion dated Jun. 18, 2015 for PCT/US2015/018112.
Office action dated Apr. 3, 2015 for CN Application No. 2012800608251.
Briggs, et al. Targeted retrieval and analysis of five Neandertal mtDNA genomes. Science. Jul. 17, 2009;325(5938):318-21. doi: 10.1126/science.1174462.
Karow. New Capture Method Enables MPI Team to Sequence Five Neandertal Mitochondrial Genomes. GenomeWeb. Jul. 21, 2009. https://www.genomeweb.com/sequencing/new-capture-method-enables-mpi-team-sequence-five-neandertal-mitochondrial-genom.
Office action dated Apr. 16, 2014 for U.S. Appl. No. 13/239,226.
Office action dated Sep. 24, 2014 for U.S. Appl. No. 13/239,226.
U.S. Appl. No. 14/390,012, filed Oct. 1, 2014, Armour et al.
Myllykangas, et al. Efficient targeted resequencing of human germline and cancer genomes by oligonucleotide-selective sequencing. Nat Biotechnol. Oct. 23, 2011;29(11):1024-7. doi: 10.1038/nbt.1996.
Singapore exam report dated Apr. 7, 2015 for SG Application No. 11201404243W.
Office action dated Jul. 9, 2015 for U.S. Appl. No. 14/211,261.
Office action dated Jul. 15, 2015 for U.S. Appl. No. 13/938,059.
Shendure, et al. Accurate multiplex polony sequencing of an evolved bacterial genome. Science. Sep. 9, 2005;309(5741):1728-32. Epub Aug. 4, 2005.
Shendure, et al. Accurate multiplex polony sequencing of an evolved bacterial genome. Science. Sep. 9, 2005;309(5741):1728-32. Epub Aug. 4, 2005. Supplemental Materials. 41 pages.
Callow, et al. Selective DNA amplification from complex genomes using universal double-sided adapters. Nucleic Acids Res. Jan. 28, 2004;32(2):e21.
European search report and opinion dated Jul. 23, 2015 for EP Application No. 13740653.
Ganova-Raeva, et al. Primer Extension Enrichment Reaction (PEER): a new subtraction method for identification of genetic differences between biological specimens. Nucleic Acids Research. 2006; 34(11):e76.
Notice of allowance dated Jul. 28, 2015 for U.S. Appl. No. 13/643,056.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
U.S. Appl. No. 14/990,339, filed Jan. 7, 2016, Amorese et al.
U.S. Appl. No. 14/991,340, filed Jan. 8, 2016, Schroeder et al.
U.S. Appl. No. 14/995,882, filed Jan. 14, 2016, Armour.
Office action dated Nov. 4, 2015 for U.S. Appl. No. 14/030,761.
U.S. Appl. No. 15/154,414, filed May 13, 2016, Armour et al.
Gu, et al. Depletion of Abundant Sequences by Hybridization (DASH): using Cas9 to remove unwanted high-abundance species in sequencing libraries and molecular counting applications. Genome Biology. 2016; 17:41. DOI: 10.1186/s13059-016-0904-5.
Oyola, et al. Efficient Depletion of Host DNA Contamination in Malaria Clinical Sequencing. J. Clin. Microbiol. Mar. 2013; 51(3):745-751.
U.S. Appl. No. 14/836,936, filed Aug. 26, 2015, Amorese et al.
U.S. Appl. No. 14/877,075, filed Oct. 7, 2015, Kurn.
U.S. Appl. No. 14/920,254, filed Oct. 22, 2015, Armour.
U.S. Appl. No. 15/047,448, filed Feb. 18, 2016, Huelga et al.
Beaucage et al. Deoxynucleoside Phosphoramidites—A New Class of Key Intermediates for Deoxypolynucleotide Synthesis. Tetrahedron Letters. 1981;22(20):1859-1862.
Bodi, et al. Comparison of Commercially Available Target Enrichment Methods for Next-Generation Sequencing. J Biomol Tech. Jul. 2013; 24(2): 73-86.
Brown, et al. Chemical synthesis and cloning of a tyrosine tRNA gene. Methods Enzymol. 1979;68:109-51.
European search report and opinion dated Jan. 29, 2016 for EP Application No. 13806978.
Froussard. A random-PCR method (rPCR) to construct whole cDNA library from low amounts of RNA. Nucleic Acids Res. Jun. 11, 1992;20(11):2900.
Gundmundsson, et al. Genome-wide association and replication studies identify four variants associated with prostate cancer susceptibility. Nat Genet. Oct. 2009;41(10):1122-6. doi: 10.1038/ng.448. Epub Sep. 20, 2009.
International search report and written opinion dated Feb. 5, 2016 for PCT/US2015/047053.
Levesque-Sergerie, et al. Detection limits of several commercial reverse transcriptase enzymes: impact on the low- and high-abundance transcript levels assessed by quantitative RT-PCR. BMC Mol Biol. Oct. 22, 2007;8:93.
Narang, et al. Improved phosphotriester method for the synthesis of gene fragments. Methods Enzymol. 1979;68:90-8.
Office action dated Apr. 4, 2016 for U.S. Appl. No. 14/995,882.
Office action dated Apr. 7, 2016 for U.S. Appl. No. 14/390,012.

(56) References Cited

OTHER PUBLICATIONS

Out, et al. Deep sequencing to reveal new variants in pooled DNA samples. Hum Mutat. Dec. 2009;30(12):1703-12. doi: 10.1002/humu.21122, abstract only.
Ovation® Target Enrichment System. User guide. Nugen. 2016. 45 pages.
Turner, et al. Massively parallel exon capture and library-free resequencing across 16 genomes. Nat Methods. May 2009;6(5):315-6. doi: 10.1038/nmeth.f.248. Epub Apr. 6, 2009.
Vater, et al. Short bioactive Spiegelmers to migraine-associated calcitonin gene-related peptide rapidly identified by a novel approach: tailored-SELEX. Nucleic Acids Res. Nov. 1, 2003;31(21):e130.
Voelkerding, et al. Next-generation sequencing: from basic research to diagnostics. Clin Chem. Apr. 2009;55(4):641-58. doi: 10.1373/clinchem.2008.112789. Epub Feb. 26, 2009.
Watson, et al. Cloning and assembly of PCR products using modified primers and DNA repair enzymes. Biotechniques. Nov. 1997;23(5):858-62, 864.
Zhang, et al. Copy number variation in human health, disease, and evolution. Annu Rev Genomics Hum Genet. 2009;10:451-81. doi: 10.1146/annurev.genom.9.081307.164217.
Zhong, et al. High-throughput illumina strand-specific RNA sequencing library preparation. Cold Spring Harb. Protoc.; 2011; 940-949. doi:10.1101/pdb.prot5652.
Gerrish, et al. Tailed pooled suppression subtractive hybridization (PSSH) adaptors do not alter efficiency. Antonie Van Leeuwenhoek. Nov. 2010;98(4):573-9. doi: 10.1007/s10482-010-9465-x. Epub Jun. 8, 2010.
Olivarius, et al. High-throughput verification of transcriptional starting sites by Deep-RACE. Biotechniques. Feb. 2009;46(2):130-2. doi: 10.2144/000113066.
Bradford, et al. A comparison of massively parallel nucleotide sequencing with oligonucleotide microarrays for global transcription profiling. BMC Genomics. May 5, 2010;11:282. doi: 10.1186/1471-2164-11-282.
European search report and opinion dated Sep. 1, 2016 for EP Application No. 14764629.3.
Hurd, et al. Advantages of next-generation sequencing versus the microarray in epigenetic research. Brief Funct Genomic Proteomic. May 2009;8(3):174-83. doi: 10.1093/bfgp/elp013. Epub Jun. 17, 2009.
Office action dated Jul. 21, 2016 for U.S. Appl. No. 14/634,326.
Office action dated Sep. 8, 2016 for U.S. Appl. No. 14/390,012.
Office Action dated Oct. 31, 2016 for European Application 13806978.6.
Stewart, et al. Complete MHC Haplotype Sequencing for Common Disease Gene Mapping. Genome Res. Jun. 2004;14(6):1176-87. Epub May 12, 2004.
Co-pending U.S. Appl. No. 14/778,564, filed Sep. 18, 2015.
Office Action dated Mar. 3, 2017 for U.S. Appl. No. 15/154,414. 13 Pages.
Office Action dated Mar. 15, 2017 for U.S. Appl. No. 14/390,012. 11 Pages.

* cited by examiner

Subtractive PCR Enrichment

Primer Directed Targeted Enrichment Of Sequences Of Interest In A Complex Library

High Efficiency Library Generation

COMPOSITIONS AND METHODS FOR TARGETED NUCLEIC ACID SEQUENCE ENRICHMENT AND HIGH EFFICIENCY LIBRARY REGENERATION

CROSS-REFERENCE

This application claims the benefit of U.S. Provisional Application No. 61/591,241, filed Jan. 26, 2012, which application is incorporated herein by reference.

BACKGROUND OF THE INVENTION

With the rapid development of next generation sequencing (NGS) technologies and platforms, whole genome sequencing is becoming increasingly feasible. Researchers are driven to generate increasing amounts of data to achieve greater understanding of variance and biological trends, and to generate data from smaller sample sizes to avoid averaging across multiple cells within a tissue.

Although the cost of whole genome sequencing is decreasing and the throughput of the NGS platforms is increasing, it is nonetheless often more practical and cost-effective to select genomic regions of interest for sequencing and analysis. Target enrichment is a commonly employed strategy in genomic DNA sequencing in which genomic regions of interest are selectively captured from a DNA sample before sequencing. Focused target enrichment is an important tool especially in the fields of study where sequencing of a large number of samples is necessary (e.g. population-based studies of disease markers or SNPs), making whole genome sequencing cost-prohibitive. Similarly, improvements have been made that enable DNA libraries to be made from nucleic acid from fewer number of cells, but these are bound by the limitations of the efficiency of ligation reactions.

Several approaches to target enrichment have been developed which vary from one another in terms of sensitivity, specificity, reproducibility, uniformity, cost and ease of use. The target enrichment methods commonly employed today can be divided into three major categories, each with its distinct advantages and disadvantages: 1) PCR-based methods; 2) capture-by-hybridization, i.e. on-array or in-solution hybrid capture; and 3) capture-by-circularization, i.e. molecular inversion probe-based methods.

The PCR-based methods employ highly parallel PCR amplification, where each target sequence in the sample has a corresponding pair of unique, sequence-specific primers. The simultaneous use of numerous primer pairs makes multiplex PCR impractical due to high level of non-specific amplification and primer-primer interactions. Recently developed microdroplet PCR technology (Tewhey et al., 2009) in which each amplification reaction is physically separated into an individual droplet removes the constraints of multiplex PCR relating to non-specific amplification and primer-primer interactions. However, microdroplet PCR and other improved PCR-based methods require special instrumentation or platforms, are limited in their throughput, and, as with conventional multiplex PCR, require a large number of individual primer pairs when enriching for a multitude of regions on interest, thus making target enrichment costly.

Hybrid capture methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture). The hybrid capture methods require complex pools of costly long oligonucleotides and long periods (typically 48 hours) of hybridization for efficient capture. For on-array hybrid capture, expensive instrumentation and hardware is also required. Because of the relatively low efficiency of the hybridization reaction, large quantities of input DNA are needed.

The molecular inversion probe (MIP) based method relies on construction of numerous single-stranded linear oligonucleotide probes, consisting of a common linker flanked by target-specific sequences. Upon annealing to a target sequence, the probe gap region is filled via polymerization and ligation, resulting in a circularized probe. The circularized probes are then released and amplified using primers directed at the common linker region. One of the main disadvantages of the MIP-based target enrichment is its relatively low capture uniformity, meaning there is large variability in sequence coverage across the target regions. As with PCR and hybrid capture, the MIP-based method requires a large number of target-specific oligonucleotides, which can be costly.

There is a need for improved methods for selective target enrichment that allow for low-cost, high throughput capture of genomic regions of interest without specialized instrumentation. Additionally, there is also a need for high efficiency nucleic acid library generation. The methods of the invention described herein fulfills these needs.

SUMMARY OF THE INVENTION

In one aspect, disclosed herein are methods for enriching for target nucleic acid sequences of interest in a sample comprising nucleic acids, the method comprising: (a) fragmenting the nucleic acids, thereby generating nucleic acid fragments; (b) appending a first adaptor to a 5' end of each nucleic acid fragment; (c) annealing one or more oligonucleotides to the nucleic acid fragments, whereby each of the one or more oligonucleotides comprise a 3' portion that is complementary to a target nucleic acid sequence of interest present in one or more of the nucleic acid fragments, and a 5' portion comprising a second adapter sequence; (d) extending the one or more oligonucleotides with a polymerase thereby generating one or more oligonucleotide extension products with the first adaptor at a first end and the second adaptor sequence at a second end; and (e) amplifying the one or more oligonucleotide extension product using a first primer that is complementary to the first adaptor and a second primer that is complementary to the second adaptor sequence to enrich for nucleic acid fragments containing the first adaptor and the second adaptor sequence at each end. In one embodiment, the method further comprises an additional step of sequencing the one or more oligonucleotide extension product following amplification. In one embodiment, the target nucleic acid sequences of interest comprise genomic DNA, RNA, or cDNA. In one embodiment, the target nucleic acid sequences of interest comprise genomic DNA. In one embodiment, the target nucleic acid sequences of interest comprise cDNA. In one embodiment, the method further comprises denaturing the nucleic acid fragments prior to step c, thereby generating single-stranded nucleic acid fragments with the first adaptor sequence at the 5' end. In one embodiment, the first adaptor can be common to each nucleic acid fragment. In one embodiment, the second adaptor sequence can be common to the one or more oligonucleotides. In one embodiment, the first adaptor and the second adaptor sequence can be distinct from each other.

In one embodiment, the first adaptor and/or the second adaptor sequence further comprise barcode sequence. In one embodiment, step b can be performed by ligation. In one embodiment, the method further comprises an additional step of performing gap repair following ligation of the first adapter to create nucleic acid fragments with complementary termini. In one embodiment, a composition comprising enriched target nucleic acid sequences of interest can be generated by the methods disclosed herein. In one embodiment, the polymerase can be a DNA polymerase.

In another aspect, disclosed herein are methods for enriching for target nucleic acid sequences of interest in a sample comprising nucleic acids, the method comprising: (a) fragmenting the nucleic acids, thereby generating nucleic acid fragments; (b) appending a first adaptor to the nucleic acid fragments wherein the first adaptor comprises a partial duplex with a short strand and a long strand wherein a 3' end of the short strand of the partial duplex adaptor comprises a blocking group, and a 5' end of the long strand of the partial duplex adaptor comprises a restriction and/or cleavage site for a nucleic acid modifying enzyme; (c) denaturing the nucleic acid fragments, thereby creating single-stranded nucleic acid fragments; (d) annealing one or more oligonucleotides to the single stranded nucleic acid fragments, whereby each of the one or more oligonucleotides comprise a sequence that is complementary to a target nucleic acid sequence of interest present in one or more of the single-stranded nucleic acid fragments, extending the one or more oligonucleotides with a polymerase to produce one or more double stranded nucleic acid complexes comprising the target nucleic acid sequences and their complements, a first end with a double stranded restriction and/or cleavage site for the nucleic acid modifying enzyme , and a second end with a 3' overhang comprising the short strand of the first adaptor; (e) cleaving the double stranded restriction and/or cleavage site with the nucleic acid modifying enzyme, thereby generating a cleavage site; (f) ligating a second adaptor to the cleavage site, wherein the second adaptor comprises a duplex with two strands; (g) denaturing the one or more double-stranded nucleic acid complexes, thereby generating one or more single stranded nucleic acid fragments comprising the target nucleic acid sequences, a strand from the second adapter at the first end, and the short strand of the first adaptor at the second end; and (h) amplifying the one or more single stranded nucleic acid fragments comprising the one or more target nucleic acid sequences with a first primer comprising sequence complementary to the strand from the second adapter and a second primer comprising sequence complementary to the short strand of the first adaptor, thereby enriching for the one or more target nucleic acid sequences. In one embodiment, the method further comprises an additional step of sequencing the one or more single stranded nucleic acid fragments from step h following amplification. In one embodiment, the target nucleic acid sequences of interest comprise genomic DNA, RNA, or cDNA. In one embodiment, the target nucleic acid sequences of interest comprise genomic DNA. In one embodiment, the target nucleic acid sequences of interest comprise cDNA. In one embodiment, the first adaptor and the second adaptor can be common to each of the nucleic acid fragments. In one embodiment, the first adaptor and the second adaptor can be distinct from each other. In one embodiment, the first adaptor and/or the second adaptor further comprise barcode sequence. In one embodiment, the double stranded restriction and/or cleavage site for the nucleic acid modifying enzyme from step e comprises the 5' end of the long strand of the partial duplex of the first adaptor and sequence complementary to the 5' end of the long strand of the partial duplex of the first adaptor generated from extension of the one or more oligonucleotides. In one embodiment, the nucleic acid modifying enzyme comprises a restriction enzyme. In one embodiment, step b can be performed by ligation. In one embodiment, a composition comprising enriched target nucleic sequences of interest can be generated by the methods disclosed herein. In one embodiment, the polymerase can be a DNA polymerase.

In yet another aspect, disclosed herein are methods for generating a library of nucleic acid sequences, the method comprising: (a) fragmenting a sample comprising nucleic acids, thereby generating nucleic acid fragments; (b) appending a first adapter to each of the nucleic acid fragments; (c) denaturing the nucleic acid fragments, thereby generating a library of single-stranded nucleic acid fragments; (d) annealing one or more oligonucleotides to the single-stranded nucleic acid fragments wherein each of the one or more oligonucleotides comprises a 3' portion complementary to sequence in one or more of the single-stranded nucleic acid fragments and a 5' portion comprising a second adaptor sequence; (e) extending the one or more oligonucleotides with a polymerase thereby generating one or more oligonucleotide extension products comprising the first adaptor at a first end and the second adapter sequence at a second end; and (f) amplifying the one or more oligonucleotide extension products with a set of primers specific to the first adaptor and the second adaptor sequence to generate a library of nucleic acid fragments comprising the first adaptor and second adaptor sequence at each end. In one embodiment, the method further comprises an additional step of performing a gap repair reaction following ligation of the forward adapter to create nucleic acid fragments with complementary termini. In one embodiment, the method further comprises an additional step of sequencing the amplified one or more oligonucleotide extension product from step f. In one embodiment, the nucleic acid sequence comprises genomic DNA. In one embodiment, the nucleic acid sequence comprises cDNA. In one embodiment, step c can be omitted wherein the nucleic acid fragments are double-stranded. In one embodiment, the 3' portion of the one or more oligonucleotides of step d comprises random sequence. In one embodiment, step b can be performed by ligation. In one embodiment, the first adaptor and the second adaptor sequence can be common to each nucleic acid fragment. In one embodiment, the first adaptor and the second adaptor sequence can be distinct from each other. In one embodiment, the first adaptor and/or the second adaptor sequence further comprise barcode sequence. In one embodiment, the methods disclosed herein can generate a composition comprising a library of nucleic sequences. In one embodiment, the polymerase can be a DNA polymerase.

In further aspect, disclosed herein are methods for enriching for target nucleic acid sequences of interest from a library comprising nucleic acid inserts with a first adaptor on a first end and a second adaptor on a second end, the method comprising: (a) denaturing the nucleic acid inserts, thereby generating a library of single stranded nucleic acid inserts; (b) annealing one or more oligonucleotides to the single stranded nucleic acid inserts, wherein each of the one or more oligonucleotides comprises a 3' portion that is complementary to a target nucleic acid sequence of interest present in one or more of the nucleic acid inserts, and a 5' portion comprising a third adaptor sequence; (c) extending the one or more oligonucleotides with a polymerase thereby generating one or more oligonucleotide extension products with the first adaptor at the first end and the third adaptor sequence at the second end; and (d) amplifying the one or more oligonucleotide extension products using a first primer that is complementary to the first adaptor and a second primer that is complementary to the third adaptor sequence to enrich for nucleic acid fragments containing the first adaptor and the third adaptor sequence at each end. In one embodiment, the method further comprises an additional step of sequencing the amplified one or more oligonucleotide extension products from step d. In one embodiment, the target nucleic acid sequences of interest comprise genomic DNA. In one embodiment, the target nucleic acid sequences of interest comprise cDNA. In one embodiment, step a can be omitted wherein the nucleic acid fragments can be double-stranded. In one embodiment, the first adaptor and the second adaptor can be common to each nucleic acid fragment. In one embodiment, the third adaptor sequence can be common to the one or more oligonucleotides. In one embodiment, the first adaptor and the second adaptor can be distinct from each other. In one embodiment, the first adaptor and the second adaptor can be the same. In one embodiment, the first adaptor, the second adaptor and/or the third adaptor sequence further comprise barcode sequence. In one embodiment, the methods disclosed herein can generate a composition comprising enriched target nucleic acid sequences of interest.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following description that sets forth illustrative embodiments, in which the principles of the invention are utilized, and the accompanying drawings of which:

DETAILED DESCRIPTION OF THE INVENTION

General

Figure 1:
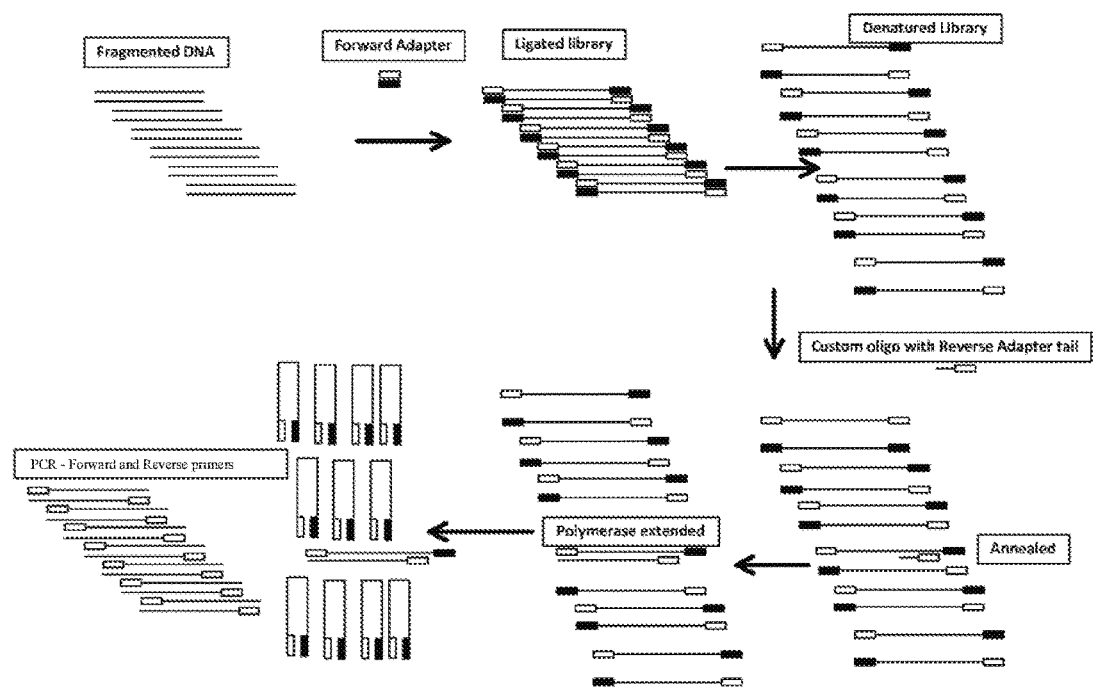
FIG. 1 depicts selective target enrichment using ligation of a single forward adaptor at the ends of the DNA fragments in the DNA library. The sequence-specific oligonucleotide that anneals to the target region of interest contains a common reverse adaptor sequence at its 5' end, and following sequence-specific oligonucleotide extension, PCR is performed using a set of primers specific to the forward and reverse adaptors.

The methods of the invention can be used for the selective enrichment of a plurality of defined target sequences from complex DNA with a set of common primers and adaptors, thus circumventing the need for multiplex PCR and multiple primer pairs. A multiplicity of target regions of interest are envisioned: for example, the regions of interest can represent all known coding regions, the entire exome, selected regions of coding genomic regions representing selected pathways, selected genomic regions known to comprise genomic variation related to altered phenotype, entire or selected regions of a specific chromosome, and the like. In another aspect, the methods of the invention can be used for high efficiency nucleic acid library production as well.

Altogether, the methods of the present invention create a simple, low cost, high throughput system for target enrichment and library preparation.

Reference will now be made in detail to exemplary embodiments of the invention. While the disclosed methods and compositions will be described in conjunction with the exemplary embodiments, it will be understood that these exemplary embodiments are not intended to limit the invention. On the contrary, the invention is intended to encompass alternatives, modifications and equivalents, which may be included in the spirit and scope of the invention.

In one embodiment, the present invention provides methods and compositions for the enrichment of specific target sequences of interest from a sample comprising nucleic acids. The methods described herein enrich target sequences using conventional duplex adaptors and/or partial duplex adaptors, sequence specific oligonucleotides, restriction enzymes and ligation. The methods further enable enrichment of target sequences from specific strands of template nucleic acids which can be further amplified using a variety of amplification methods. In another embodiment, the present invention provides methods for high efficiency generation of libraries comprising specific nucleic acid sequences of interest.

In one embodiment, the present invention provides methods and compositions for the enrichment of target nucleic acid sequences from a sample comprising nucleic acids. In one aspect, the method comprises fragmenting nucleic acids in an input sample to generate nucleic acid fragments. The nucleic acids can be DNA, or RNA. The nucleic acids can be single or double stranded. The DNA can be genomic DNA or cDNA or any combination thereof. In one embodiment, the nucleic acids in an input sample are double stranded DNA. In one embodiment, fragmentation of the nucleic acids can be achieved through methods known in the art. Fragmentation can be through physical fragmentation methods and/or enzymatic fragmentation methods. Physical fragmentation methods can include nebulization, sonication, and/or hydrodynamic shearing. In some embodiments, the fragmentation can be accomplished mechanically comprising subjecting the nucleic acids in the input sample to acoustic sonication. In some embodiments, the fragmentation comprises treating the nucleic acids in the input sample with one or more enzymes under conditions suitable for the one or more enzymes to generate double-stranded nucleic acid breaks. Examples of enzymes useful in the generation of nucleic acid or polynucleotide fragments include sequence specific and non-sequence specific nucleases. Non-limiting examples of nucleases include DNase I, Fragmentase, restriction endonucleases, variants thereof, and combinations thereof. Reagents for carrying out enzymatic fragmentation reactions are commercially available (e.g, from New England Biolabs). For example, digestion with DNase I can induce random double-stranded breaks in DNA in the absence of $Mg^{++}$ and in the presence of $Mn^{++}$. In some embodiments, fragmentation comprises treating the nucleic acids in the input sample with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. In some embodiments, the method includes the step of size selecting the fragments via standard methods known in the art such as column purification or isolation from an agarose gel.

In some embodiments, the nucleic acids in the input sample can be fragmented into a population of fragmented nucleic acid molecules or polynucleotides of one or more specific size range(s). In some embodiments, the fragments have an average length from about 10 to about 10,000 nucleotides. In some embodiments, the fragments have an average length from about 50 to about 2,000 nucleotides. In some embodiments, the fragments have an average length from about 100-2,500, 10-1,000, 10-800, 10-500, 50-500, 50-250, or 50-150 nucleotides. In some embodiments, the fragments have an average length less than 10,000 nucleotide, such as less than 5,000 nucleotides, less than 2,500 nucleotides, less than 2,500 nucleotides, less than 1,000 nucleotides, less than 500 nucleotides, such as less than 400 nucleotides, less than 300 nucleotides, less than 200 nucleotides, or less than 150 nucleotides.

In one embodiment, fragmentation of the nucleic acids can be followed by end repair of the nucleic acid fragments. End repair can include the generation of blunt ends, non-blunt ends (i.e sticky or cohesive ends), or single base overhangs such as the addition of a single dA nucleotide to the 3'-end of the nucleic acid fragments, by a polymerase lacking 3'-exonuclease activity. End repair can be performed using any number of enzymes and/or methods known in the art including, but not limited to, commercially available kits such as the Encore™ Ultra Low Input NGS Library System I. In a preferred embodiment, end repair can be performed on double stranded DNA fragments to produce blunt ends wherein the double stranded DNA fragments contain 5' phosphates and 3' hydroxyls. In some embodiments, the double-stranded DNA fragments can be blunt-end polished (or "end repaired") to produce DNA fragments having blunt ends, prior to being joined to adapters. Generation of the blunt ends on the double stranded fragments can be generated by the use of a single strand specific DNA exonuclease such as for example exonuclease 1, exonuclease 7 or a combination thereof to degrade overhanging single stranded ends of the double stranded products. Alternatively, the double stranded DNA fragments can be blunt ended by the use of a single stranded specific DNA endonuclease, for example, but not limited to, mung bean endonuclease or S1 endonuclease. Alternatively, the double stranded products can be blunt ended by the use of a polymerase that comprises single stranded exonuclease activity such as for example T4 DNA polymerase, or any other polymerase comprising single stranded exonuclease activity or a combination thereof to degrade the overhanging single stranded ends of the double stranded products. In some cases, the polymerase comprising single stranded exonuclease activity can be incubated in a reaction mixture that does or does not comprise one or more dNTPs. In other cases, a combination of single stranded nucleic acid specific exonucleases and one or more polymerases can be used to blunt end the double stranded fragments generated by fragmenting the sample comprising nucleic acids. In still other cases, the nucleic acid fragments can be made blunt ended by filling in the overhanging single stranded ends of the double stranded fragments. For example, the fragments may be incubated with a polymerase such as T4 DNA polymerase or Klenow polymerase or a combination thereof in the presence of one or more dNTPs to fill in the single stranded portions of the double stranded fragments. Alternatively, the double stranded DNA fragments can be made blunt by a combination of a single stranded overhang degradation reaction using exonucleases and/or polymerases, and a fill-in reaction using one or more polymerases in the presence of one or more dNTPs.

In some embodiments, the 5' and/or 3' end nucleotide sequences of fragmented nucleic acids are not modified or end-repaired prior to ligation with the adapter oligonucleotides of the present invention. For example, fragmentation by a restriction endonuclease can be used to leave a predictable overhang, followed by ligation with one or more adapter oligonucleotides comprising an overhang complementary to the predictable overhang on a nucleic acid fragment. In another example, cleavage by an enzyme that leaves a predictable blunt end can be followed by ligation of blunt-ended nucleic acid fragments to adapter oligonucleotides comprising a blunt end. In some embodiments, end repair can be followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. Nucleic acid fragments having an overhang can be joined to one or more adapter oligonucleotides having a complementary overhang, such as in a ligation reaction. For example, a single adenine can be added to the 3' ends of end repaired DNA fragments using a template independent polymerase, followed by ligation to one or more adapters each having a thymine at a 3' end. In some embodiments, adapter oligonucleotides can be joined to blunt end double-stranded nucleic acid fragments which have been modified by extension of the 3' end with one or more nucleotides followed by 5' phosphorylation. In some cases, extension of the 3' end can be performed with a polymerase such as for example Klenow polymerase or any of the suitable polymerases provided herein, or by use of a terminal deoxynucleotide transferase, in the presence of one or more dNTPs in a suitable buffer containing magnesium. In some embodiments, nucleic acid fragments having blunt ends can be joined to one or more adapters comprising a blunt end. Phosphorylation of 5' ends of nucleic acid fragments can be performed for example with T4 polynucleotide kinase in a suitable buffer containing ATP and magnesium. The fragmented nucleic acid molecules may optionally be treated to dephosphorylate 5' ends or 3' ends, for example, by using enzymes known in the art, such as phosphatases.

The methods described herein for enriching for target nucleic acid sequences further comprise appending a first adaptor to the nucleic acid fragments generated by the methods described herein. In one embodiment, the first adaptor can be a forward adaptor. Appending the first adaptor to the nucleic acid fragments generated by methods described herein can be achieved using a ligation reaction or a priming reaction. In one embodiment, appendage of a first adaptor to the nucleic acid fragments comprises ligation. In one embodiment, ligation of the first adaptor to the nucleic acid fragments can be following end repair of the nucleic acid fragments. In another embodiment, the ligation of the first adaptor to the nucleic acid fragments can be following generation of the nucleic acid fragments without end repair of the nucleic acid fragments. The first adaptor can be any type of adaptor known in the art including, but not limited to, conventional duplex or double stranded adaptors in which the adaptor comprises two complementary strands. In a preferred embodiment, the first adaptor can be a double stranded DNA adaptor. In one embodiment, the first adaptor can be an oligonucleotide of known sequence and, thus, allow generation and/or use of sequence specific primers for amplification and/or sequencing of any polynucleotides to which the first adaptor(s) is appended or attached. In one embodiment, the first adaptor can be a conventional duplex adaptor, wherein the first adaptor comprises sequence well known in the art. In a preferred embodiment, the first adaptor can be appended to the nucleic acid fragments generated by the methods described herein in multiple orientations. In a preferred embodiment, the methods described herein can involve the use of a first duplex adaptor comprising double stranded DNA of known sequence that is blunt ended and can bind to the double stranded nucleic acid fragments generated by the methods described herein in one of two orientations. In one embodiment, the first adaptor can be ligated to each of the nucleic acid fragments such that each of the nucleic acid fragments comprises the same first adaptor. In other words, each of the nucleic acid fragments comprises a common first adaptor. In another embodiment, a first adaptor can be appended or ligated to a library of nucleic acid fragments generated by the methods described herein such that each nucleic acid fragment in the library of nucleic acid fragments comprises the first adaptor ligated to one or both ends.

In one embodiment, the first adaptor can be ligated or appended to the 5' and/or 3' ends of the nucleic acid fragments generated by the methods described herein. The first adaptor can comprise two strands wherein each strand comprises a free 3' hydroxyl group but neither strand comprises a free 5' phosphate. In one embodiment, the free 3' hydroxyl group on each strand of the first adaptor can be ligated to a free 5' phosphate present on either end of the nucleic acid fragments of the present invention. In this embodiment, the first adaptor comprises a ligation strand and a non-ligation strand whereby the ligation strand can be ligated to the 5'phosphate on either end of the nucleic acid fragment while a nick or gap can be present between the non-ligation strand of the first adaptor and the 3' hydroxyl on either end of the nucleic acid fragment. In one embodiment, the nick or gap can be filled in by performing a gap repair reaction. In one embodiment, the gap repair can be performed with a DNA dependent DNA polymerase with strand displacement activity. In one embodiment, the gap repair can be performed using a DNA dependent DNA polymerase with weak or no strand displacement activity. In one embodiment, the ligation strand of the first adaptor can serve as the template for the gap repair or fill-in reaction. In this embodiment, the gap repair or fill-in reaction comprises an extension reaction wherein the ligation strand of the first adaptor serves as a template and leads to the generation of nucleic acid fragments with complementary termini or ends as depicted, for example, in FIG. 1. In one embodiment, the gap repair can be performed using Taq DNA polymerase. In one embodiment, the ligation of the first adaptor to the nucleic acid fragments generated by the methods described herein may not be followed gap repair as depicted, for example, in FIG. 2. In this embodiment, the nucleic acid fragments comprise first adaptor sequence ligated only at the 5' end of each strand.

Ligation and, optionally gap repair, of the first adaptor to the nucleic acid fragments generates a first adaptor-nucleic acid fragment complex. In one embodiment, the first adaptor-nucleic acid fragment complex can be denatured. Denaturation can be achieved using any of the methods known in the art including, but not limited to, physical, thermal, and/or chemical denaturation. In one embodiment, denaturation can be achieved using thermal or heat denaturation. In one embodiment, denaturation of the first adaptor-nucleic acid fragment complex generates single stranded nucleic acid fragments comprising first adaptor sequence at only the 5'end of the nucleic acid fragments as depicted, for example, in FIG. 2. In another embodiment, denaturation of the first adaptor-nucleic acid fragment complex generates single stranded nucleic acid fragments comprising first adaptor sequence at both the 5'end and 3'end of the nucleic acid fragments as depicted, for example, in FIG. 1.

In one embodiment, the nucleic acid fragments comprising first adaptor sequence appended to either the 5' end or both the 5' and 3' end can be denatured to generate single stranded nucleic acid fragments comprising first adaptor sequence appended to either the 5' end or both the 5' and 3' end. In one embodiment, the methods of the present invention described herein can be used to generate a plurality of single stranded nucleic acid fragments comprising first adaptor sequence appended to either the 5' end or both the 5' and 3' end. In one embodiment, an oligonucleotide comprising at a first end sequence complementary to a target sequence of interest present in a single stranded nucleic acid fragment and at a second end sequence from a second adaptor , wherein the second adaptor sequence is not complementary to the target nucleic acid can be annealed to the single stranded nucleic acid fragments. In one embodiment, the second adaptor sequence can be sequence from a reverse adaptor. In one embodiment, the target nucleic acid sequence of interest can be present in one or more of the single stranded nucleic acid fragments. In one embodiment, different or distinct target nucleic acid sequences of interest can be present in one or more of the single stranded nucleic acid fragments. In one embodiment, one or more oligonucleotides can comprise sequence complementary to the same sequence of interest present in one or more single stranded nucleic acid fragments. In this embodiment, the one or more oligonucleotides can comprise sequence that is complementary to different parts or regions of the same sequence of interest. In one embodiment, the different regions can be adjacent to each other. In one embodiment, the different regions can be non-adjacent to each other. In a preferred embodiment, the one or more oligonucleotides that comprise sequence complementary to the same target nucleic acid sequence of interest further comprise the same second adaptor sequence. In another embodiment, one or more oligonucleotides can comprise sequence complementary to different or distinct sequences of interest which can be present in one or more single stranded nucleic acid fragments. In a preferred embodiment, the one or more oligonucleotides that comprise sequence complementary to different or distinct target nucleic acid sequences of interest further comprise the same second adaptor sequence. In one embodiment, the sequence complementary to the target sequence of interest can be at the 3'end of the oligonucleotide and the second adaptor sequence can be at the 5'end of the oligonucleotide. In a preferred embodiment, the second adaptor sequence is non-complementary to the target nucleic acid sequence of interest. In this manner, the second adaptor sequence serves as a tail. The second adaptor sequence can be a conventional adaptor sequence. In a preferred embodiment, the second adaptor sequence can be a conventional adaptor sequence that is different than or distinct from the sequence of the first adaptor appended to the single stranded nucleic acid fragment as described above. In one embodiment, the second adaptor sequence can be of known sequence and, thus, allow generation and/or use of sequence specific primers for amplification and/or sequencing of any polynucleotides to which the second adaptor sequence is appended or attached. In a separate embodiment, the oligonucleotide can be annealed to the nucleic acid fragments comprising the first adaptor sequence appended to either the 5' end or both the 5' and 3' end without prior denaturation. In this embodiment, annealing of the oligonucleotide can be via formation of a triple helix or triplex between the oligonucleotide and a double stranded nucleic acid fragment comprising the first adaptor sequence appended to either the 5' end or both the 5' and 3' ends of the double stranded nucleic acid fragment. In this embodiment, the double stranded nucleic acid fragment comprises a sequence of interest and can be present amongst a plurality of double stranded nucleic acid fragments comprising first adaptor sequence appended to either the 5' end or both the 5' and 3' end. Further to this embodiment, the oligonucleotide comprises sequence complementary to the sequence of interest in the double stranded nucleic acid fragment. Overall, the use of the oligonucleotide comprising sequence complementary to a target sequence of interest present in a nucleic acid fragment amongst one or more or a plurality of nucleic acid fragments allows for selective binding and subsequent enrichment of said nucleic fragment using the methods described herein.

Following annealing of the oligonucleotide as described above, a polymerase can be used to extend the oligonucleotide. In one embodiment, the polymerase can be a DNA dependent DNA polymerase. In one embodiment, the DNA dependent DNA polymerase can be any of the DNA dependent DNA polymerases as described herein and extension of the oligonucleotide can be by any of the methods known in the art. In one embodiment, an oligonucleotide comprising the second adaptor sequence, wherein the second adaptor sequence is not complementary to the target nucleic acid, and sequence complementary to a target sequence of interest present in a nucleic acid fragment comprising a first adaptor appended to one and/or both ends can be annealed to the nucleic acid fragment and extended with a polymerase to generate an oligonucleotide extension product comprising the first adaptor sequence at a first end and the second adaptor sequence at a second end. In one embodiment, the nucleic acid fragment can be present amongst a plurality of nucleic acid fragments comprising first adaptor appended to one and/or both ends. In this embodiment, the oligonucleotide extension product can only be generated for a nucleic acid fragment that contains the target sequence of interest.

In one embodiment, the oligonucleotide extension product generated by the methods described herein can be subjected to an amplification reaction. In one embodiment, the amplification reaction can be exponential, and may be carried out at various temperature cycles or isothermal. In one embodiment, the amplification can be polymerase chain reaction. In one embodiment, the amplification reaction can be isothermal. In one embodiment, the oligonucleotide extension product comprises first adaptor sequence on one end and second adaptor sequence on the other end as generated by the methods described herein. In a preferred embodiment, the oligonucleotide extension product can be separated from the template nucleic acid fragment in order to generate a single stranded oligonucleotide extension product with first adaptor sequence on the 5' end and second adaptor sequence on the 3' end. The single stranded oligonucleotide extension product can then be amplified using a first primer comprising sequence complementary to the first adaptor and a second primer comprising sequence complementary to the second adaptor sequence. In this manner only oligonucleotide extension products comprising both the first and the second adaptor sequence will be amplified and thus enriched. In one embodiment, the first adaptor and/or the second adaptor sequence can comprise an identifier sequence. In one embodiment, the identifier sequence can be barcode sequence. In one embodiment, the barcode sequence can be the same or different for the first adaptor and the second adaptor sequence. In one embodiment, the first adaptor and/or the second adaptor sequence can comprise sequence that can be used for downstream applications such as, for example, but not limited to, sequencing. In one embodiment, the first adaptor and/or the second adaptor sequence can comprise flow cell sequences which can be used for sequencing with the sequencing method developed by Illumina and described herein.

Figure 4:
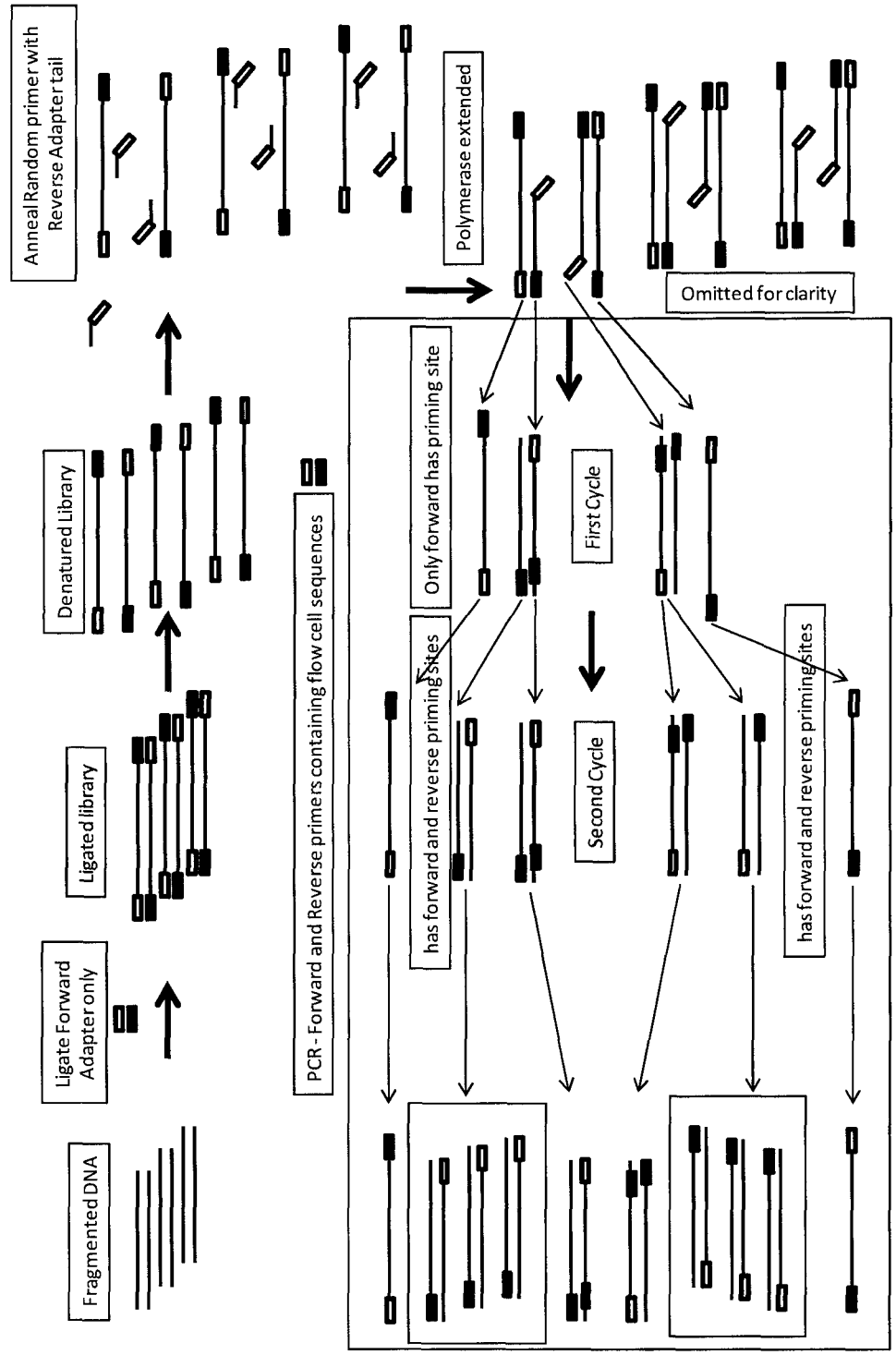
FIG. 4 depicts high efficiency NGS library generation using random priming. The oligonucleotide that anneals to the DNA fragment contains a common reverse adaptor sequence at its 5' end, and following primer extension, PCR is performed using a set of primers specific to the forward and reverse adaptors.

In an alternate embodiment, the methods of the present invention can be used to generate a library of nucleic acid fragments or inserts wherein each nucleic acid fragment comprises an adaptor at one or both ends. In one embodiment, the adaptors can be present at both ends and can be distinct from each other. In one embodiment, the adaptors can be present at both ends and can comprise the same adaptor sequence. The generation of the library comprising nucleic acid inserts with distinct adaptors at both ends can involve the methods for generating oligonucleotide extension products comprising first adaptor sequence on one end and second adaptor sequence on the other end as described above with the exception that the oligonucleotide that binds to the nucleic acid fragments and can be extended comprises random sequence. In this embodiment, the oligonucleotide comprises random sequence at the 3' portion that is hybridizable to one or more nucleic acid fragments and further comprises second adaptor sequence at the 5'-portion. Extension of the oligonucleotide along the nucleic acid fragment and the corresponding first adaptor generates a product, or products, comprising the second adaptor at one end and a sequence complementary to the first adaptor at the other end, as illustrated in FIG. 4. In one embodiment, the random sequence present in the oligonucleotide can bind to and be extended on one or more nucleic acid inserts. In one embodiment, one or more oligonucleotides comprising a 3' portion comprising random sequence and a 5' portion comprising second adaptor sequence can be annealed to a library comprising nucleic acid inserts comprising a first adaptor sequence on one or both ends of each of the nucleic acid inserts. In one embodiment, the first adaptor can be the same or common to each of the nucleic acid inserts. In one embodiment, the second adaptor sequence can be the same or common to each of the one or more oligonucleotides. In one embodiment, the methods described above can be used to generate a library of nucleic acid inserts comprising wherein each of the nucleic acid inserts comprises a common first adaptor on one end and a common second adaptor sequence on a second end. In one embodiment, the first adaptor and the second adaptor sequence can be distinct from each other. In one embodiment, the first adaptor and the second adaptor sequence can comprise the same adaptor sequence. Overall, the methods of the present invention as described above can be used for the high efficiency generation of a library of nucleic acid sequences.

In yet another alternate embodiment to the methods of the invention as described above, the first adaptor can be a double stranded DNA adaptor comprising a partial duplex, wherein the two strands of the adaptor can be different lengths with a complementary region and an overhanging region at the 5' end. In this embodiment, the 5' end of the long strand of the partial duplex adaptor can comprise a unique site for a nucleic acid modifying enzyme, such as a restriction enzyme, that is absent from the short strand of the duplex adaptor. In a further embodiment, the 3' end of the short strand adaptor can be modified by a replacement of the 3' OH-group by a blocking group, for example, a dideoxynucleotide (ddCMP, ddAMP, ddTMP, or ddGMP) to prevent polymerase extension. In this embodiment, the first adaptor comprising the partial duplex can be ligated to nucleic acid fragments generated by the methods described herein. In one embodiment, ligation of the partial duplex first adaptor can be followed by a gap repair reaction as described above. In this embodiment, ligation of the partial duplex first adaptor is not followed by a gap repair reaction. In a preferred embodiment, the partial duplex first adaptor comprises a free 5' phosphate on the short strand and a free 3'hydroxyl on the long strand. In this embodiment, ligation of the partial duplex adaptor generates double stranded nucleic acid fragments wherein both ends of the double stranded nucleic acid fragment comprise the long strand and short strand of the partial duplex first adaptor. A double stranded partial duplex first adaptor-nucleic acid fragment complex can be generated by ligation. In one embodiment, the double stranded partial duplex first adaptor-nucleic acid fragment complex can be denatured to generate a single stranded nucleic acid fragment comprising the long strand of the first adaptor on a first end and the short strand of the first adaptor on a second end. In this embodiment, the first end is the 5' end and the second end is the 3' end. In one embodiment, the first adaptor can be appended to one or more nucleic acid fragments as generated by the methods described herein such that each of the nucleic acid fragments comprises the same first adaptor or, in other words, the first adaptor can be common to each of the nucleic acid inserts. An oligonucleotide or primer comprising sequence complementary to a sequence of interest in the single stranded nucleic acid fragment can be annealed to the single stranded nucleic acid fragment and extended using a polymerase. In one embodiment, the polymerase can be a DNA dependent DNA polymerase. In one embodiment, the DNA dependent DNA polymerase can be any of the DNA dependent DNA polymerases as described herein and extension of the oligonucleotide can be by any of the methods known in the art. Extension of the primer annealed to the single stranded nucleic acid fragment generates an oligonucleotide extension product comprising sequence complementary to the long strand of the first adaptor on one end. In one embodiment, the oligonucleotide extension product remains hybridized to the single stranded nucleic acid fragment such that the restriction and/or cleavage site specific for a nucleic acid modifying enzyme is made double stranded. The double stranded site can then be cleaved by the nucleic acid modifying enzyme specific for the double stranded restriction site. In one embodiment, the nucleic acid modifying enzyme can be a restriction enzyme. In one embodiment, the restriction enzyme can be specific for a double stranded restriction site. In one embodiment, cleavage of the restriction site can generate a blunt end or non-blunt end. In one embodiment, end repair by any of the methods described herein can be performed on the end of the nucleic acid fragment following cleavage. Cleavage of the restriction and/or cleavage site generates a site to which a second adaptor can be ligated. Ligation of the second adaptor can be through any of the methods for ligation as described herein. In one embodiment, ligation generates a double stranded nucleic acid fragment comprising the second adaptor on a first end and a partial duplex on a second end, wherein the partial duplex comprises a 3' overhang comprising the sequence of the short strand of the first adaptor. The double stranded nucleic acid fragment can then be denatured using any of the methods for denaturation disclosed herein to generate a single stranded nucleic acid fragment comprising the second adaptor sequence on the first end and the sequence of the short strand of the first adaptor on the second end. In one embodiment, the first end and second end comprise the 5' end and 3' end, respectively. In one embodiment, the second adaptor can be appended to one or more nucleic acid fragments following cleavage of the double stranded restriction site such that each of the nucleic acid fragments comprises the same second adaptor or, in other words, the second adaptor can be common to each of the nucleic acid inserts. The single stranded nucleic acid fragment can then be amplified using a first primer specific for the second primer and a second primer specific for sequence present in the short strand of the first adaptor. In one embodiment, the amplification reaction can be exponential, and may be carried out at various temperature cycles or isothermal. In one embodiment, the amplification can be polymerase chain reaction. In one embodiment, the amplification reaction can be isothermal. Overall, only a fragment comprising the second adaptor and the short strand of the first adaptor will be amplified or enriched. In so far as the method provides for enrichment of targeted fragments of the library, and not enrichment of oligonucleotide extension products generated by the extension of the oligonucleotide comprising sequence complementary to a target sequence of interest, there is no distortion of the original DNA library, and the enrichment is independent of the insert length. Because the 3' end of the short strand of the partial duplex adaptor is 3' blocked, the method enables directional or asymmetric ligation. In one embodiment, the oligonucleotide that comprises sequence complementary to a sequence of interest in a nucleic acid fragment further comprises reverse adaptor sequence. In this embodiment, the sequence complementary to a sequence of interest in the nucleic acid fragment can be present in a 3' portion of the oligonucleotide and the reverse adaptor sequence can be present at a 5' portion. Further to this embodiment, the reverse adaptor sequence can be a common or conventional adaptor sequence and can be different or distinct from the first and/or second adaptors. Further still to this embodiment, the methods described above can lead to the generation of a single stranded nucleic acid fragment comprising the second adaptor at one end and the reverse adaptor sequence at the other end. Subsequent to this embodiment, the single stranded nucleic acid fragment can be enriched through amplification using a first primer specific to the second adaptor and a second primer specific to the third adaptor sequence.

The methods of the inventions are further applicable to any enrichment of target nucleic acid sequences of interest from libraries comprising fragments of nucleic acid of a sample appended with adaptor sequence at one or both ends, wherein the libraries are generated using ligation of the adaptor or adaptor sequences to one or both ends as described herein or by ligation independent methods, such as for example Nextera, a transposome driven method. In one embodiment, the nucleic acid can be DNA such as genomic DNA or cDNA. In one embodiment, the nucleic acid can be double stranded. Enrichment of nucleic acid sequences of interest can be achieved using the methods described herein for target enrichment. In one embodiment, the method for enriching for target nucleic acid sequences of interest from a library comprising nucleic inserts with adaptors appended to one or both ends comprises denaturing the nucleic acid inserts to generate a library of single stranded nucleic acid inserts. In one embodiment, each of the nucleic acid inserts can comprise a first adaptor sequence on one end and a second adaptor sequence on an opposite end. In one embodiment, the first adaptor and the second adaptor can be distinct from each other. In one embodiment, the first adaptor and the second adaptor can comprise the same adaptor sequence. In one embodiment, each of the nucleic acid inserts can comprise a first adaptor sequence on one end and a second adaptor sequence on an opposite end such that denaturation generates a library of single stranded nucleic acid inserts comprising the first adaptor sequence on one end and the second adaptor sequence on an opposite end. Denaturation can be achieved using any of the methods described herein. Further to the embodiments described above, one or more oligonucleotides can be annealed to the single stranded nucleic acid inserts. In one embodiment, each of the one or more oligonucleotides comprises a 3' portion that is complementary to a target nucleic acid sequence of interest present in one or more of the nucleic acid inserts, and a 5' portion comprising a third adaptor sequence. In one embodiment, the third adaptor sequence is distinct from either or both of the first adaptor and the second adaptor. The one or more oligonucleotides can be extended with a polymerase (i.e. a DNA polymerase) thereby generating one or more oligonucleotide extension products with the first or second adaptor at a first end and the third adaptor sequence at a second end. In one embodiment, the first end comprises the 5' end and the second end comprises the 3' end. The one or more oligonucleotide extension products can be amplified using a first primer that can be complementary to the first or second adaptor and a second primer that can be complementary to the third adaptor sequence to enrich for nucleic acid fragments comprising the first or second adaptor and the third adaptor sequence at each end. In one embodiment, the first and second adaptors can be common to each of the nucleic acid inserts in the library. In one embodiment, the third adaptor sequence can be common to each of the one or more oligonucleotides. Overall, the target enrichment methods as described above can be used to generate a composition comprising a library of nucleic acid inserts enriched for any target sequence of interest from a non-enriched library comprised of nucleic acid inserts with an adaptor ligated to one or both ends.

A schematic of a preferred embodiment of the methods described herein for enriching for target sequences of interest is illustrated in FIG. 1. Overall, FIG. 1 depicts a method for isolating or enriching for a nucleic acid fragment or insert comprising a target nucleic acid sequence from a library or plurality of nucleic acid fragments. The method in FIG. 1 involves generation of a ligated library of nucleic acid fragments or inserts wherein each fragment or insert of the ligated library comprises a common forward adaptor and a fragment or insert specific reverse adaptor distinct from the forward adaptor such that subtractive PCR using a primer directed against the common forward adaptor and a primer directed against the reverse adaptor enriches for a nucleic acid fragment or insert comprising a target nucleic acid sequence. The input for the method depicted in FIG.1 is fragmented DNA. The fragmented DNA is double stranded and comprises a plurality or library of DNA fragments. In one embodiment, the DNA fragments can be derived from complex DNA, such as double-stranded DNA, genomic DNA or mixed DNA from more than one organism. In one embodiment, the DNA fragments can be derived from RNA that has been converted to cDNA through a first strand synthesis reaction using any of the methods well known in the art for generating cDNA from an RNA template which can include, but is not limited to, combining the RNA with a primer (i.e. random primer), and reverse transcribing the RNA template with an RNA-dependent DNA polymerase. In one embodiment, the DNA fragments can be derived from RNA that has been converted to double stranded cDNA through a first and second strand synthesis reaction using any of the methods well known in the art. Fragmentation of the DNA to produce the DNA fragments can be achieved through any of the methods described herein for fragmenting nucleic acids which can include, but are not limited to, physical (i.e. sonication), and/or chemical (i.e. restriction enzyme treatment) fragmentation reactions.

As depicted in FIG. 1, a single forward adaptor is ligated to the DNA fragments. In one embodiment, the single forward adaptor can comprise known sequence. In one embodiment, the single forward adaptor can be a common adaptor. In one embodiment, the DNA fragments can be subjected to an end repair reaction as described herein to produce blunt ends. In this embodiment, the single forward adaptor can also comprise blunt ends and ligation between the single forward adaptor and the DNA fragments can be through blunt end ligation as described herein. Ligation can be facilitated through the use of enzymes (i.e. T4 DNA ligase) and methods known in the art, including, but not limited to, commercially available kits such as the Encore™ Ultra Low Input NGS Library System. In FIG. 1, the forward adaptor can contain a strand (the ligation strand) that ligates with the free 5'phosphate on a 5' end of the DNA fragments and a strand that does not ligate (non-ligation strand) to a 3' end of the DNA fragments. In one embodiment, the ligation reaction can lead to the generation of a nick or gap between the non-ligation strand of the single forward adaptor and the 3' end of the DNA fragments. In this embodiment, the nick or gap can be repaired or filled in through a gap repair or fill-in reaction wherein the 3' end of the DNA fragments can be extended with a polymerase (preferably with a DNA dependent DNA polymerase such as Taq DNA polymerase) wherein the ligation strand of the forward adaptor can serve as template. In this embodiment, the gap repair generates DNA fragments with complementary ends. As depicted in FIG. 1, the DNA fragments with complementary ends are denatured to generate a denatured library comprising single stranded DNA fragments with complementary ends. Denaturation can be achieved using any of the methods known in the art which can include, but are not limited to, heat denaturation, and/or chemical denaturation.

As depicted in FIG. 1, a custom oligonucleotide with a reverse adaptor tail is annealed to the single stranded DNA fragments with complementary ends. In one embodiment, the custom oligonucleotide with a reverse adaptor tail can comprise a 3' portion comprising sequence complementary to a target sequence of interest in one of the single-stranded DNA fragments and a 5' portion comprising reverse adaptor sequence that is not complementary to the single-stranded DNA fragments in the denatured library. In one embodiment, the reverse adaptor sequence can be known sequence.

In a preferred embodiment, the reverse adaptor sequence can be distinct from the single forward adaptor as described herein. In one embodiment, a plurality of custom oligonucleotides with a reverse adaptor tail can be added to the denatured library wherein the plurality of custom oligonucleotides with a reverse adaptor tail comprise a 3' portion comprising sequence complementary to a target sequence of interest in one or more of the single-stranded DNA fragments of the denatured library and a 5' portion comprising a reverse adaptor sequence that is not complementary to the single-stranded DNA fragments in the denatured library. In one embodiment, the reverse adaptor tail comprises the same reverse adaptor sequence in each of the plurality of custom oligonucleotides with a reverse adaptor tail, and wherein the reverse adaptor sequence is distinct from the forward adaptor sequence. In another embodiment, the reverse adaptor tail comprises a different reverse adaptor sequence for each of the plurality of custom oligonucleotides with a reverse adaptor tail, and wherein each of the different reverse adaptor sequences is distinct from the forward adaptor sequence. In one embodiment, the 3' portion of the custom oligonucleotide with a reverse adaptor tail can be a specific sequence, wherein the custom oligonucleotide comprises a sequence complementary to the target sequence of interest and provides a means for targeted enrichment of sequence or sequences of interest using the methods of the invention. In another embodiment the 3' portion of the custom oligonucleotide with reverse adaptor tail can be a randomly generated sequence hybridizable to random sequences of the library of fragments with adaptor sequences on one or both ends, providing means for efficient, non-enriched library generation employing the methods of the invention.

Following annealing of the custom oligonucleotide with a reverse adaptor tail to a sequence of interest in a single-stranded DNA fragment of the denatured library, the custom oligonucleotide with a reverse adaptor tail is extended using any method known in the art, which can include but is not limited to, extension using a DNA dependent DNA polymerase using the single stranded DNA fragment of the denatured library as a template. Extension of the custom oligonucleotide with a reverse adaptor tail generates an oligonucleotide extension product with forward adaptor sequence at one end and reverse adaptor sequence at the other end. In this embodiment, the custom oligonucleotide with a reverse adaptor tail can only anneal to and be extended on DNA fragments in the denatured library comprising the target sequence of interest for which the custom oligonucleotide with a reverse adaptor tail is directed. As illustrated in FIG. 1, a subtractive polymerase chain reaction (PCR) procedure is subsequently performed using a first primer directed against the forward adaptor sequence and a second primer directed toward the reverse adaptor sequence such that only the oligonucleotide extension product with the forward adaptor sequence at one end and the reverse adaptor sequence at the other end can be amplified and thus enriched.

Figure 2:
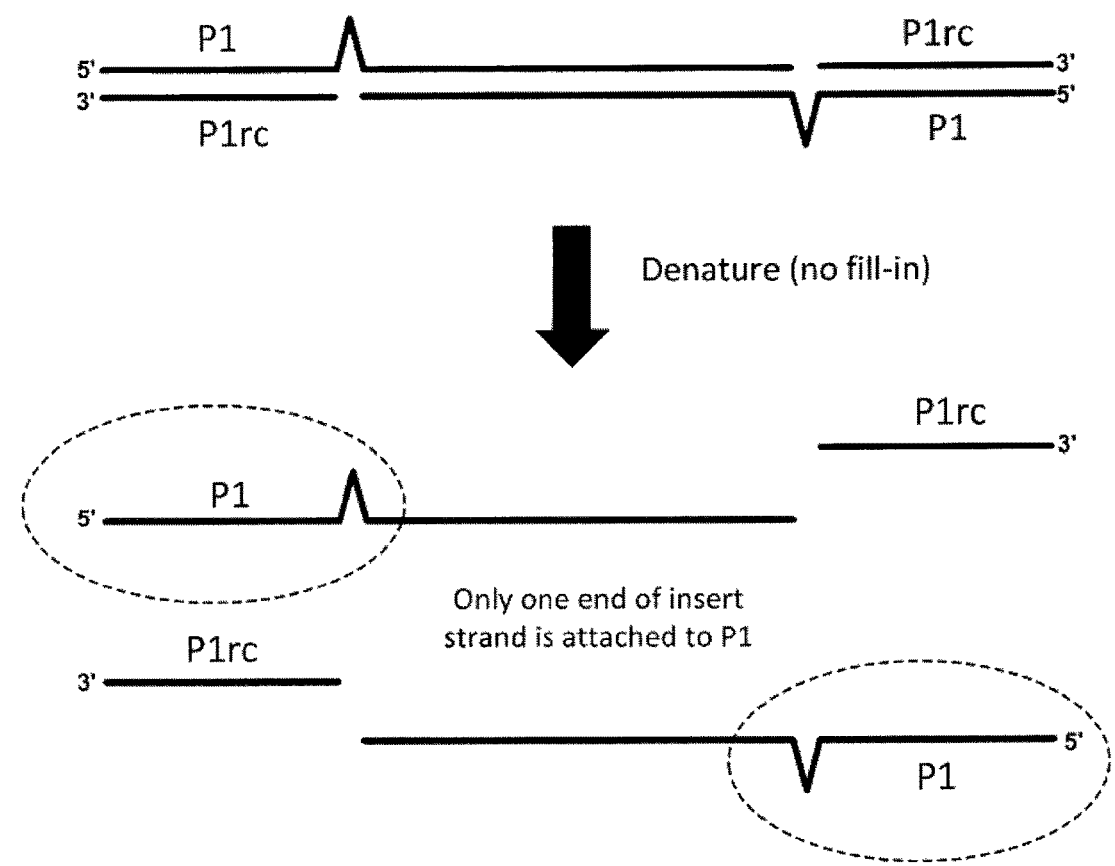
FIG. 2 depicts an alternative ligation protocol wherein the DNA-fragment-adaptor complex is denatured following ligation without nick repair and adaptor fill-in, generating ligation products where non-complementary ends exist on each insert.

FIG. 2 depicts another embodiment of subtractive PCR enrichment method as described for FIG. 1, wherein ligation of a duplex forward adaptor (P1) to a double stranded nucleic acid fragment is not subjected to gap repair. The duplex forward adaptor (P1) comprises a strand (the ligation strand; P1) that ligates with the free 5'phosphate on a 5' end of the nucleic acid fragment and a strand that does not ligate (non-ligation strand; P1rc) to a 3' end of the nucleic acid fragment. In this embodiment, the ligation strand is ligated to the 5' end of both strands of a double stranded nucleic fragment whereas a gap or nick is generated between the non-ligation strand and the 3'end of both strands of the double stranded nucleic acid fragment. As depicted in FIG. 2, the ligation of the P1 adaptor to the nucleic acid fragment is followed by denaturation without a gap repair or fill-in reaction thereby generating a single stranded nucleic acid fragment with non-complementary ends. In this embodiment, the single stranded nucleic acid fragment with non-complementary ends comprises a P1 forward adaptor sequence at a 5' end and fragment specific sequence at a 3' end. In a further embodiment, the single stranded nucleic fragment with non-complementary ends can be further processed as described above and illustrated in FIG. 1 to generate a single stranded nucleic fragment with the P1 forward adaptor sequence at the 5' end and a distinct reverse adaptor sequence on the 3' end.

FIG. 4 illustrates another embodiment of the present invention for the high efficiency generation of libraries comprising nucleic acid fragments with distinct adaptors on each end. In this embodiment, the methods for generating a denatured library comprising single stranded DNA fragments with a single forward adaptor sequence on a 5' end and a reverse adaptor sequence on a 3' end is similar to the method described for FIG. 1. However, in FIG. 4, an oligonucleotide with a reverse adaptor tail is used whereby the oligonucleotide comprises a 3' portion comprising random sequence and a reverse adaptor tail wherein the reverse adaptor tail comprises reverse adaptor sequence that is distinct from the single forward adaptor sequence. As illustrated in FIG. 4, PCR can be carried out with a first primer directed against the single forward adaptor sequence and a second primer directed toward the reverse adaptor sequence wherein both the first and second primers further comprise flow cell sequences. In this manner, single stranded DNA fragments with a single forward adaptor sequence on a 5' end and a reverse adaptor sequence on a 3' end comprise flow cell sequences that can be used to adhere the amplified single stranded DNA fragments to flow cells for subsequent sequencing by the method commercialized by Illumina, as described U.S. Pat. Nos. 5,750,341; 6,306,597; and 5,969,119.

Figure 3:
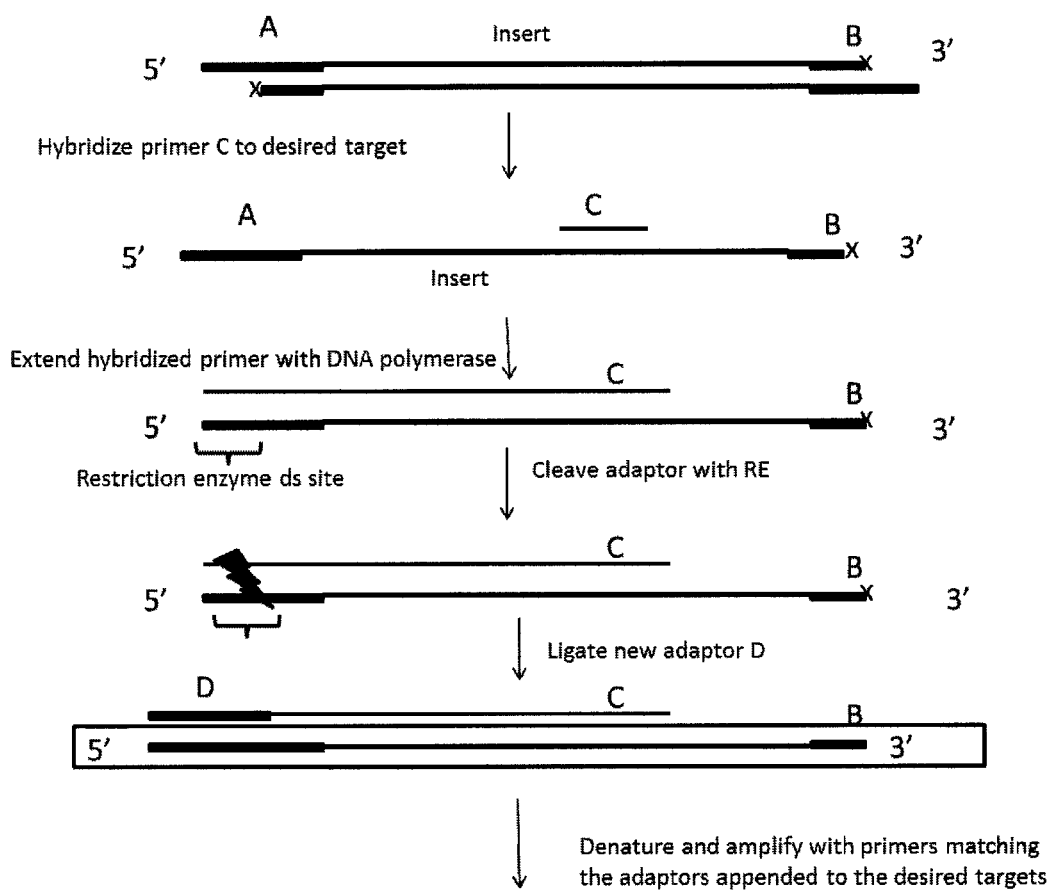
FIG. 3 depicts selective target enrichment using ligation of partial duplex adaptors. Cleavage of the 5' end of the long strand of the partial duplex adaptor (and the corresponding complementary sequence of the extended sequence-specific oligonucleotide) by a nucleic acid modifying enzyme specific for double-stranded DNA allows for ligation of a new adaptor pair, and consequently, amplification with primers corresponding to the new adaptors.

FIG. 3 illustrates a method for enrichment of a target nucleic acid sequence, or sequences of interest, contained in a double stranded nucleic acid insert from a complex library. In one embodiment, the complex library comprises nucleic acid inserts from a genomic DNA sample, In FIG. 3, the single forward adaptor comprises a partial duplex forward adaptor comprising a long strand, A, that forms a partial duplex with a short strand, B. Strand A of the partial duplex adaptor further comprises a restriction enzyme site while strand B does not contain the restriction enzyme site. Strand B further comprises a blocking group wherein the 3' end of strand B is modified by replacement of the 3' OH group with a blocking group that can prevent polymerase extension. In one embodiment, the partial duplex forward adaptor is ligated to the double stranded nucleic acid fragments such that a double stranded insert with the partial duplex forward adaptor appended to both ends is generated. In this embodiment, the 5' end of strand B of the partial duplex adaptor can contain a free 5' phosphate which can be ligated to a free 3' OH present on one or both strands of the double stranded insert. Subsequent denaturation generates a single stranded insert comprising sequence A on a 5'end and strand B on a 3' end. A primer, C, directed against a specific sequence of interest within the single stranded insert can be annealed to the specific sequence and extended with a DNA polymerase using the single stranded insert as a template. In one embodiment, primer C can be a sequence specific primer and is employed for enrichment of target, or targets, of interest according to the methods of the invention. In one embodiment, primer C can be a random primer. Extension of primer C with DNA polymerase generates an extended primer C product that comprises sequence complementary to sequence A at its' 3' end in a double stranded complex with the template insert strand such that a double stranded restriction site has been generated between sequence A and its' complement. In one embodiment, the double stranded restriction enzyme recognition site can be cleaved by a restriction enzyme specific for the double stranded restriction site thereby generating a truncated, or cleaved, adaptor sequence at one end. A second forward adaptor comprising a common, or conventional, duplex adaptor D is then ligated to the cleavage site using any of the ligation methods described herein, thereby generating a double stranded complex comprising the second forward adaptor D at one end and a 3' overhang comprising strand B on the opposite end. The double stranded complex comprising the second forward adaptor D at one end and a 3' overhang comprising strand B on the opposite end is denatured and amplified using a first primer directed against the second forward adaptor D and a second primer directed against strand B. In this manner, the methods depicted in FIG. 3 can be used to enrich for specific sequences of interest from a complex library since the methods are designed such that the second forward adaptor D can only bind to the double stranded cleavage site generated by restriction enzyme digestion of the double stranded restriction site created between sequence A and its complement following extension of primer C. As described, primer C can be directed against a target sequence of interest present in a single, or multiple insert, or inserts, amongst a plurality of inserts. Moreover, the method can be made strand specific by designing primer C to bind to target sequence of interest present on one strand or the other of an insert in an amongst a plurality of inserts.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W. H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Input Nucleic Acid

The input can be a nucleic acid. In one embodiment, the input can be DNA. In one embodiment, the input nucleic acid can be complex DNA, such as double-stranded DNA, genomic DNA or mixed DNA from more than one organism. In one embodiment, the input can be RNA. In one embodiment, the RNA can be obtained and purified using standard techniques in the art and include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA may include snoRNAs, microRNAs, siRNAs, piRNAs and long nc RNAs. In one embodiment, the input nucleic acid can be cDNA. The cDNA can be generated from RNA, e.g., mRNA. The cDNA can be single or double stranded. The input DNA can be of a specific species, for example, human, rat, mouse, other animals, specific plants, bacteria, algae, viruses, and the like. The input complex also can be from a mixture of genomes of different species such as host-pathogen, bacterial populations and the like. The input DNA can be cDNA made from a mixture of genomes of different species. Alternatively, the input nucleic acid can be from a synthetic source. The input DNA can be mitochondrial DNA. The input DNA can be cell-free DNA. The cell-free DNA can be obtained from, e.g., a serum or plasma sample. The input DNA can comprise one or more chromosomes. For example, if the input DNA is from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The DNA can be plasmid DNA, cosmid DNA, bacterial artificial chromosome (BAC), or yeast artificial chromosome (YAC). The input DNA can be from more than one individual or organism. The input DNA can be double stranded or single stranded. The input DNA can be part of chromatin. The input DNA can be associated with histones.

In some embodiments, the oligonucleotides targeting the selected sequence regions of interest are designed to hybridize to single-stranded nucleic acid targets. In one embodiment, the oligonucleotides targeting the selected sequence regions of interest are designed to hybridize to single-stranded DNA targets. In the case where the input nucleic acid sample comprises genomic DNA or other double-stranded DNA, the input nucleic acid sample can be first denatured to render the target single stranded and enable hybridization of the oligonucleotides to the desired sequence regions of interest. In these embodiments, the methods and compositions described herein can allow for region-specific enrichment and amplification of sequence regions of interest. In some embodiments, the other double-stranded DNA can be double-stranded cDNA generated by first and second strand synthesis of one or more target RNAs.

In other embodiments, the oligonucleotides targeting the selected sequence regions of interest are designed to hybridize to double-stranded nucleic acid targets, without denaturation of the double stranded nucleic acids. In other embodiments, the oligonucleotides targeting the selected sequence regions of interest are designed to hybridize to a double-stranded DNA target, without denaturation of the dsDNA. In these embodiments, the oligonucleotides targeting the selected sequence regions of interest are designed to form a triple helix (triplex) at the selected sequence regions of interest. The hybridization of the oligonucleotides to the double-stranded DNA sequence regions of interest can be carried out without prior denaturation of the double stranded nucleic acid sample. In such embodiments, the methods and compositions described herein can allow for region-specific enrichment as well as strand-specific enrichment and amplification of sequence regions of interest. This method can be useful for generation of copies of strand specific sequence regions of interest from complex nucleic acid without the need to denature the dsDNA input DNA, thus enabling enrichment and analysis of multiplicity of sequence regions of interest in the native complex nucleic acid sample. The method can find use for studies and analyses carried out in situ, enable studies and analysis of complex genomic DNA in single cells or collection of very small well defined cell population, as well as permit the analysis of complex genomic DNA without disruption of chromatin structures.

A "target nucleic acid sequence" or "target sequence" as used herein, is a polynucleotide sequence of interest, for which enrichment is desired. The target sequence may be known or not known, in terms of its actual sequence.

Generally, a "template", as used herein, is a polynucleotide that contains the target nucleic acid sequence. The terms "target sequence," "target nucleic acid sequence," "target nucleotide sequence," "regions of interest," or "sequence of interest" and, variations thereof, are used interchangeably.
Oligonucleotides of the Invention As used within the invention, the term "oligonucleotide" refers to a polynucleotide chain, typically less than 200 residues long, most typically between 15 and 100 nucleotides long, but also intended to encompass longer polynucleotide chains. Oligonucleotides may be single-or double-stranded. As used in this invention, the term "oligonucleotide" may be used interchangeably with the terms "primer" and "adaptor".

As used herein, the terms "hybridization"! "hybridizing" and "annealing" are used interchangeably and refer to the pairing of complementary nucleic acids.

The term "primer", as used herein, can refer to a nucleotide sequence, generally with a free 3' hydroxyl group, that is capable of hybridizing with a template (such as one or more target polynucleotides, one or more target DNAs, one or more target RNAs or a primer extension product) and is also capable of promoting polymerization of a polynucleotide complementary to the template. A primer can be, for example, an oligonucleotide. It can also be, for example, a sequence of the template (such as a primer extension product or a fragment of the template created following RNase [i.e. RNase H] cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer. A primer may contain a non-hybridizing sequence that constitutes a tail of the primer. A primer may still be hybridizing to a target even though its sequences are not fully complementary to the target.

The primers of the invention are generally oligonucleotides that are employed in an extension reaction by a polymerase along a polynucleotide template, such as in PCR, SPIA or cDNA synthesis, for example. The oligonucleotide primer can be a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, preferably 90%, more preferably 95%, most preferably 100%, complementarity to a sequence or primer binding site.

"Complementary", as used herein, can refer to complementarity to all or only to a portion of a sequence. The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 or 12 to about 200 nucleotides, usually about 20 to about 50 nucleotides. In general, the target polynucleotide is larger than the oligonucleotide primer or primers as described previously.

In some cases, the identity of the investigated target polynucleotide sequence is known, and hybridizable sequence specific oligonucleotides or primers can be synthesized precisely according to the antisense sequence of the aforesaid target polynucleotide sequence. In some embodiments, multiple sequence-specific oligonucleotides or primers are employed to hybridize to a multiplicity of genomic regions of interest, allowing for selective enrichment of the regions of interest. In so far as the genomic regions may be very long, multiple oligonucleotides can be designed to hybridize to different sequence regions within the genomic regions of interest. In other embodiments, when the target polynucleotide sequence is unknown, the hybridizable sequence of an oligonucleotide or primer is a random sequence. Oligonucleotides or primers comprising random sequences may be referred to as "random primers", or "random oligonucleoties," as described herein. In one embodiment, an oligonucleotide or primer of the present invention hybridizable to a target sequence may comprise a mixture of primers or oilognucleotides designed to hybridize to a plurality (e.g. 2, 3, 4, about 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, 25,000 or more) of target sequences. In some cases, the plurality of target sequences may comprise a group of related sequences, random sequences, a whole transcriptome or fraction (e.g. substantial fraction) thereof, or any group of sequences such as mRNA. In some embodiments, the primers can be directed to known sequences present in the adaptors used in the invention as described herein. In this embodiment, the primers can comprise groups of primers comprising one or more primers in each group, wherein each group of primers can be directed against distinct adaptors.

Tailed primers or oligonucleotides can be employed in certain embodiments of the invention. In general, a tailed primer comprises a 3' portion that is hybridizable to one or more target polynucleotides, and a 5' portion that is not hybridizable to the one or more target polynucleotides. In general, the non-hybridizable 5' portion does not hybridize to the one or more target polynucleotides under conditions in which the hybridizable 3' portion of the tailed primer hybridizes to the one or more target polynucleotides. In some embodiments, the non-hybridizable 5' portion comprises an adaptor sequence. In some embodiments, the non-hybridizable 5' portion comprises a common or conventional adaptor sequence. In some embodiments, the non-hybridizable 5' portion comprises a common or conventional adaptor sequence that is distinct or different from the sequence of other adaptors used in the present invention. In some embodiments, the non-hybridizable 5' portion comprises a promoter-specific sequence. Generally, a promoter-specific sequence comprises a single-stranded DNA sequence region which, in double-stranded form is capable of mediating RNA transcription. Examples of promoter-specific sequences are known in the art, and include, without limitation, T7, T3, or SP6 RNA polymerase promoter sequences. When the tailed primer is extended with a DNA polymerase, a primer extension product with a 5' portion comprising a defined sequence can be created. This primer extension product can then have a second primer anneal to it, which can be extended with a DNA polymerase to create a double stranded product comprising a defined sequence at one end. In some embodiments, where the non-hybridizable 5' portion of one or more tailed primers comprises a promoter-specific sequence, creation of a double-stranded product comprising a defined sequence at one end generates a double-stranded promoter sequence that is capable of mediating RNA transcription. In some embodiments, a double-stranded promoter sequence can be generated by hybridizing to the promoter-specific sequence an oligonucleotide comprising a sequence complementary to the promoter-specific sequence. In some embodiments, formation of a double-stranded promoter can be followed by the generation of single-stranded RNA by RNA transcription of sequence downstream of the double-stranded promoter, generally in a reaction mixture comprising all necessary components, including but not limited to ribonucleoside triphosphates (rNTPs) and a DNA-dependent RNA polymerase. Tailed primers can comprise DNA, RNA, or both DNA and RNA. In some embodiments, the tailed primer consists of DNA.

Composite primers can be employed in certain embodiments of the invention. Composite primers are primers that are composed of RNA and DNA portions. In some aspects, the composite primer can be a tailed composite primer comprising, for example, a 3'-DNA portion and a 5'-RNA portion. In the tailed composite primer, a 3'-portion, all or a portion of which comprises DNA, is complementary to a polynucleotide; and a 5'-portion, all or a portion of which comprises RNA, is not complementary to the polynucleotide and does not hybridize to the polynucleotide under conditions in which the 3'-portion of the tailed composite primer hybridizes to the polynucleotide target. When the tailed composite primer is extended with a DNA polymerase, a primer extension product with a 5'-RNA portion comprising a defined sequence can be created. This primer extension product can then have a second primer anneal to it, which can be extended with a DNA polymerase to create a double stranded product with an RNA/DNA heteroduplex comprising a defined sequence at one end. The RNA portion can be selectively cleaved from the partial heteroduplex to create a double-stranded DNA with a 3'-single-stranded overhang which can be useful for various aspects of the present invention including allowing for isothermal amplification using a composite amplification primer.

A "random primer," as used herein, can be a primer that generally comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. A random primer will generally be an oligonucleotide or a population of oligonucleotides comprising a random sequence(s) in which the nucleotides at a given position on the oligonucleotide can be any of the four nucleotides, or any of a selected group of the four nucleotides (for example only three of the four nucleotides, or only two of the four nucleotides). In some cases all of the positions of the oligonucleotide or population of oligonucleotides can be any of two or more nucleotides. In other cases, only a portion of the oligonucleotide, for instance a particular region, will comprise positions which can be any of two or more bases. In some cases, the portion of the oligonucleotide which comprises positions which can be any of two or more bases is about 5, 6, 7, 8, 9, 10, 11, 12, 13, 14, or about 15-20 nucleotides in length. In some cases, a random primer may comprise a tailed primer having a 3'-region that comprises a random sequence and a 5'-region that is a non-hybridizing sequence that comprises a specific, non-random sequence. The 3'-region may also comprise a random sequence in combination with a region that comprises poly-T sequences. The sequence of a random primer (or its complement) may or may not be naturally-occurring, or may or may not be present in a pool of sequences in a sample of interest. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide or target nucleic sequence which does not require prior knowledge of the exact sequence of the target. In some embodiments one portion of a primer is random, and another portion of the primer comprises a defined sequence. For example, in some embodiments, a 3'-portion of the primer will comprise a random sequence, while the 5'-portion of the primer comprises a defined sequence. In some embodiments a 3'-random portion of the primer will comprise DNA, and a 5'- defined portion of the primer will comprise RNA, in other embodiments, both the 3' and 5'-portions will comprise DNA. In some embodiments, the 5'-portion will contain a defined sequence and the 3'-portion will comprise a poly-dT sequence that is hybridizable to a multiplicity of RNAs in a sample (such as all mRNA). In some embodiments, a "random primer," or primer comprising a randomly generated sequence, comprises a collection of primers comprising one or more nucleotides selected at random from two or more different nucleotides, such that all possible sequence combinations of the nucleotides selected at random may be represented in the collection. In some embodiments, generation of one or more random primers does not include a step of excluding or selecting certain sequences or nucleotide combinations from the possible sequence combinations in the random portion of the one or more random primers.

In one embodiment, the oligonucleotides of the invention can be tailed oligonucleotides. In one embodiment, the 5'-tail can comprise RNA and is non hybridizable to the RNA in the sample. In one embodiment, the 5'-tail can comprise DNA and is non hybridizable to the DNA in the sample. In one embodiment, the 5'-tail can comprise an adaptor that is not hybridizable to the DNA and/or nucleic acid fragments derived from the sample comprising nucleic acid. In one embodiment, the 5'-tail can comprise an adaptor sequence that is not hydridizable to the DNA and/or nucleic acid fragments derived from the sample comprising nucleic acid. In some embodiments, the 5'-tail can comprise a common adaptor sequence that is not hydridizable to the DNA and is distinct from any other adaptor or adaptor sequence used in the methods of the invention described herein. In some embodiments, the 5'-tail can comprise an identifier sequence. In some embodiments, the identifier sequence can comprise a barcode sequence. In some embodiments, the 5'-tail can comprise a common adaptor sequence that is not hydridizable to the DNA and a barcode sequence.

The term "adaptor", as used herein, refers to an oligonucleotide of known sequence, the ligation of which to a target polynucleotide or a target polynucleotide strand of interest enables the generation of amplification-ready products of the target polynucleotide or the target polynucleotide strand of interest. The target polynucleotide molecules may be fragmented or not prior to the addition of adaptors.

Various adaptor designs are envisioned which are suitable for generation of amplification-ready products of target sequence regions/strands of interest. For example, the two strands of the adaptor may be self-complementary, non-complementary or partially complementary. A common feature of the adaptors depicted in FIG. 3 of the invention is the partial duplex design, wherein the two strands of the adaptor are different lengths with a complementary region and an overhanging region at the 5' end. The 5' end of the long strand of the partial duplex adaptor contains a unique site for a nucleic acid modifying enzyme, such as a restriction enzyme, that is absent from the short strand of the duplex adaptor. The 3' end of the short strand adaptor is modified by a replacement of the 3' OH-group is by a blocking group, for example, a dideoxynucleotide (ddCMP, ddAMP, ddTMP, or ddGMP) to prevent polymerase extension.

In some embodiments of the invention, the adaptors comprise an additional identifier sequence, i.e. a barcode sequence. As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, each barcode in a plurality of barcodes differ from every other barcode in the plurality at at least three nucleotide positions, such as at least 3, 4, 5, 6, 7, 8, 9, 10, or more positions. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, both the forward and reverse adapter comprise at least one of a plurality of barcode sequences. In some embodiments, the first, second, and/or third adaptor comprises at least one of a plurality of barcode sequences. In some embodiments, each reverse adapter comprises at least one of a plurality of barcode sequences, wherein each barcode sequence of the plurality of barcode sequences differs from every other barcode sequence in the plurality of barcode sequences. In some embodiments, both the first adapter and the second adapter comprise at least one of a plurality of barcode sequences. In some embodiments, barcodes for second adapter oligonucleotides are selected independently from barcodes for first adapter oligonucleotides. In some embodiments, first adapter oligonucleotides and second adapter oligonucleotides having barcodes are paired, such that adapters of the pair comprise the same or different one or more barcodes. In some embodiments, the methods of the invention further comprise identifying the sample from which a target polynucleotide is derived based on the barcode sequence to which the target polynucleotide is joined. In general, a barcode comprises a nucleic acid sequence that when joined to a target polynucleotide serves as an identifier of the sample from which the target polynucleotide was derived.

Recently, many improvements have been made in adaptor design that have reduced the occurrence of adapter dimer. These improvements include the use of nucleotide analogs and structured oligonucleotides, and have allowed for use of higher concentrations of oligonucleotides in ligation reactions. The higher concentrations of adapters in ligation reactions have enabled researchers to produce high quality libraries from as few as 150 copies of genome. Ligation of adaptors to the ends of DNA fragments, in particular those fragments containing the regions of interest is suitable for carrying out the methods of the invention. Various ligation modalities are envisioned, dependent on the choice of nucleic acid modifying enzymes and the resulting double-stranded DNA cleavage. For example, when a blunt end product comprising the target region/sequence of interest is generated, blunt end ligation can be suitable. Alternatively, where the cleavage is carried out using a restriction enzyme of known sequence specificity, leading to the generation of cleavage sites with known sequence overhangs, suitable ends of the adaptors can be designed to enable hybridization of the adaptor to the cleavage site of the sequence region of interest and subsequent ligation. Reagents and methods for efficient and rapid ligation of adaptors are commercially available and are known in the art.

Nucleic Acid Modifying Enzymes

The nucleic acid (NA)-modifying enzyme can be DNA-specific modifying enzyme. The NA-modifying enzyme can be selected for specificity for double-stranded DNA. The enzyme can be a duplex-specific endonuclease, a blunt-end frequent cutter restriction enzyme, or other restriction enzyme. Examples of blunt-end cutters include DraI or SmaI. The NA-modifying enzyme can be an enzyme provided by New England Biolabs. The NA-modifying enzyme can be a homing endonuclease (a homing endonuclease can be an endonuclease that does not have a stringently-defined recognition sequence). The NA-modifying enzyme can be a nicking endonuclease (a nicking endonuclease can be an endonuclease that can cleave only one strand of DNA in a double-stranded DNA substrate). The NA-modifying enzyme can be a high fidelity endonuclease (a high fidelity endonuclease can be an engineered endonuclease that has less "star activity" than the wild-type version of the endonuclease).

In a preferred embodiment, the NA-modifying enzyme is a sequence and duplex-specific, DNA modifying enzyme.

DNA-Dependent DNA Polymerases DNA-dependent DNA polymerases for use in the methods and compositions of the invention are capable of effecting extension of a primer or oligonucleotide according to the methods of the invention. In one embodiment, a preferred DNA-dependent DNA polymerase can be one that is capable of extending a nucleic acid primer in the presence of the DNA and/or cDNA template. Exemplary DNA dependent DNA polymerases suitable for the methods of the present invention include but are not limited to Klenow polymerase, with or without 3'-exonuclease, Bst DNA polymerase, Bca polymerase, .phi.29 DNA polymerase, Vent polymerase, Deep Vent polymerase, Taq polymerase, T4 polymerase, and E. coli DNA polymerase 1, derivatives thereof, or mixture of polymerases. In some cases, the polymerase does not comprise a 5'-exonuclease activity. In other cases, the polymerase comprises 5' exonuclease activity. In some cases, the primer or oligonucleotide extension of the present invention may be performed using a polymerase comprising strong strand displacement activity such as for example Bst polymerase. In other cases, the primer extension of the present invention may be performed using a polymerase comprising weak or no strand displacement activity. One skilled in the art may recognize the advantages and disadvantages of the use of strand displacement activity during the primer extension step, and which polymerases may be expected to provide strand displacement activity (see e.g., New England Biolabs Polymerases).

Methods of Amplification

The methods, compositions and kits described herein can be useful to generate amplification-ready products for downstream applications such as massively parallel sequencing (i.e. next generation sequencing methods), generation of libraries with enriched population of sequence regions of interest, or hybridization platforms. Methods of amplification are well known in the art. Suitable amplification reactions can be exponential or isothermal and can include any DNA amplification reaction, including but not limited to polymerase chain reaction (PCR), strand displacement amplification (SDA), linear amplification, multiple displacement amplification (MDA), rolling circle amplification (RCA), single primer isothermal amplification (SPIA, see e.g. U.S. Pat. No. 6,251,639), Ribo-SPIA, or a combination thereof. In some cases, the amplification methods for providing the template nucleic acid may be performed under limiting conditions such that only a few rounds of amplification (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.), such as for example as is commonly done for cDNA generation. The number of rounds of amplification can be about 1-30, 1-20, 1-15, 1-10, 5-30, 10-30, 15-30, 20-30, 10-30, 15-30, 20-30, or 25-30.

PCR is an in vitro amplification procedure based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

LCR uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

SDA (Westin et a 2000, Nature Biotechnology, 18, 199-202; Walker et al 1992, Nucleic Acids Research, 20, 7, 1691-1696), is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Some aspects of the invention utilize linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some embodiments, the amplification is exponential, e.g. in the enzymatic amplification of specific double stranded sequences of DNA by a polymerase chain reaction (PCR). In other embodiments the amplification method is linear. In other embodiments the amplification method is isothermal.

Downstream Applications

An important aspect of the invention is that the methods and compositions disclosed herein can be efficiently and cost-effectively utilized for downstream analyses, such as next generation sequencing or hybridization platforms, with minimal loss of biological material of interest. The methods of the present invention can also be used in the analysis of genetic information of selective genomic regions of interest (e.g., analysis of SNPs or other disease markers) as well as genomic regions which may interact with the selective region of interest.

Sequencing

For example, the methods of the invention are useful for sequencing by the method commercialized by Illumina, as described U.S. Pat. Nos. 5,750,341; 6,306,597; and 5,969,119. In general, double stranded fragment polynucleotides can be prepared by the methods of the present invention to produce amplified nucleic acid sequences tagged at one (e.g., (A)/(A') or both ends (e.g., (A)/(A') and (C)/(C')). In some cases, single stranded nucleic acid tagged at one or both ends is amplified by the methods of the present invention (e.g., by SPIA or linear PCR). The resulting nucleic acid is then denatured and the single-stranded amplified polynucleotides are randomly attached to the inside surface of flow-cell channels. Unlabeled nucleotides are added to initiate solid-phase bridge amplification to produce dense clusters of double-stranded DNA. To initiate the first base sequencing cycle, four labeled reversible terminators, primers, and DNA polymerase are added. After laser excitation, fluorescence from each cluster on the flow cell is imaged. The identity of the first base for each cluster is then recorded. Cycles of sequencing are performed to determine the fragment sequence one base at a time.

In some embodiments, the methods of the invention are useful for preparing target polynucleotides for sequencing by the sequencing by ligation methods commercialized by Applied Biosystems (e.g., SOLiD sequencing). In other embodiments, the methods are useful for preparing target polynucleotides for sequencing by synthesis using the methods commercialized by 454/Roche Life Sciences, including but not limited to the methods and apparatus described in Margulies et al., *Nature*(2005) 437:376-380 (2005); and U.S. Pat. Nos. 7,244,559; 7,335,762; 7,211,390; 7,244,567; 7,264,929; and 7,323,305. In other embodiments, the methods are useful for preparing target polynucleotide(s) for sequencing by the methods commercialized by Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods are useful for preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

Another example of a sequencing technique that can be used in the methods of the provided invention is nanopore sequencing (see e.g. Soni G V and Meller A. (2007) *Clin Chem* 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Another example of a sequencing technique that can be used in the methods of the provided invention is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Genetic Analysis

The methods of the present invention can be used in the analysis of genetic information of selective genomic regions of interest as well as genomic regions which may interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present invention can be used to amplify target nucleic acid of interest for DNA hybridization studies to determine the presence or absence of polymorphisms. The polymorphisms, or alleles, can be associated with diseases or conditions such as genetic disease. In other cases the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

Kits

Any of the compositions described herein may be comprised in a kit. In a non-limiting example, the kit, in a suitable container, comprises: an adaptor or several adaptors, one or more of oligonucleotide primers and reagents for ligation, primer extension and amplification. The kit may also comprise means for purification, such as a bead suspension.

The containers of the kits will generally include at least one vial, test tube, flask, bottle, syringe or other containers, into which a component may be placed, and preferably, suitably aliquotted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

A kit will preferably include instructions for employing, the kit components as well the use of any other reagent not included in the kit. Instructions may include variations that can be implemented.

In one aspect, the invention provides kits containing any one or more of the elements disclosed in the above methods and compositions. In some embodiments, a kit comprises a composition of the invention, in one or more containers. In some embodiments, the invention provides kits comprising adapters, primers, and/or other oligonucleotides described herein. In some embodiments, the kit further comprises one or more of: (a) a DNA ligase, (b) a DNA-dependent DNA polymerase, (c) an RNA-dependent DNA polymerase, (d) a forward adapter (e) one or more oligonucleotides comprising reverse adaptor sequence and (f) one or more buffers suitable for one or more of the elements contained in said kit. The adapters, primers, other oligonucleotides, and reagents can be, without limitation, any of those described above. Elements of the kit can further be provided, without limitation, in any of the amounts and/or combinations (such as in the same kit or same container) described above. The kits may further comprise additional agents, such as those described above, for use according to the methods of the invention. For example, the kit can comprise a first forward adaptor that is a partial duplex adaptor as described herein, a second forward adapter, and a nucleic acid modifying enzyme specific for a restriction and/or cleavage site present in the first forward adaptor. The kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained.

In one embodiment, the kit comprises a plurality of forward adaptor oligonucleotides, wherein each of said forward adaptor oligonucleotides comprises at least one of a plurality of barcode sequences, wherein each barcode sequence of the plurality of barcode sequences differs from every other barcode sequence in said plurality of barcode sequences at at least three nucleotide positions, and instructions for using the same. Forward adapters comprising different barcode sequences can be supplied individually or in combination with one or more additional forward adapters having a different barcode sequence. In some embodiments, the kit can comprises a plurality of first and second forward adapter oligonucleotides. Second forward adapter oligonucleotides can be supplied separately from or in combination with one or more first forward adapters, and/or one or more different second adapters. Combinations of first and second forward adapters can be supplied in accordance with combinations described above. In some embodiments, the kit can comprises a plurality of oligonucleotides comprising reverse adaptor sequence. In one embodiment, the kit can comprises a plurality of oligonucleotides comprising reverse adaptor sequence, wherein each of the plurality of oligonucleotides comprising reverse adaptor sequence further comprises sequence complementary to a specific target sequence of interest present in a nucleic acid. In one embodiment, the kit can comprises a plurality of oligonucleotides comprising reverse adaptor sequence, wherein each of the plurality of oligonucleotides comprising reverse adaptor sequence further comprises random sequence. In one embodiment, the kit comprises a plurality of oligonucleotides with reverse adaptor sequence, wherein each of said oligonucleotides with reverse adaptor sequence comprises at least one of a plurality of barcode sequences, wherein each barcode sequence of the plurality of barcode sequences differs from every other barcode sequence in said plurality of barcode sequences at at least three nucleotide positions, and instructions for using the same. Oligonucleotides with reverse adaptor sequence comprising different barcode sequences can be supplied individually or in combination with one or more additional oligonucleotides with reverse adaptor sequence having a different barcode sequence.

Products Based on the Methods of the Invention

Products based on the methods of the invention may be commercialized by the Applicants under the trade name Ovation®. Ovation® is a trademark of NuGEN Technologies, Inc.

EXAMPLES

Example 1

Characterization of the Human Oral Microbiome by Selective Enrichment of Bacterial 16S Ribosomal DNA Sequences Sample Nucleic Acid Microbial genomic DNA is isolated from human saliva using the OMNIgene-DISCOVER sample collection kit (DNA Genotek) according to the manufacturer's instructions. Extracted DNA is then fragmented via sonication to an average length of 400 by and purified using Agencourt AMPure XP beads (Beckman Coulter Genomics).

Generation of control and Test Libraries with Ligated Forward Adaptors

The NuGEN Ovation Ultralow Library System (NuGEN Technologies) is used to generate two next generation sequencing libraries from 100 ng of the purified sample. The first library, an unenriched control, is made as recommended by the manufacturer. A second 'test' library, the input for downstream enrichment steps, is generated using the same library construction kit modified as follows. Briefly, DNA is blunted and prepared for ligation under the standard end-repair reaction conditions described in the kit. Fragments are then ligated to the forward adaptor only. As depicted in FIG. 2, ligation attaches the forward adaptor to each end of each DNA fragment, leaving a single-strand nick on the opposite strand. Adaptor fill-in will be performed, thus generating ligation products where complementary ends exist on each insert.

Ligation products of at least 100 by in length are purified by selective binding to Agencourt AMPure XP beads and taken forward into the enrichment process.

Amplification

Ribosomal DNA fragments from the test library are selectively amplified with two distinct steps: 1) gene-specific primer extension; and 2) PCR with universal adaptor sequences. The primer extension step is performed with oligonucleotides containing a 3' gene-specific region and a 5'common region that contains a portion of the Illumina reverse adaptor sequence. Consensus 16S sequences making up the gene-specific segment are selected by comparing the ribosomal operons from 40 diverse bacterial species using the ClustalW multiple sequence alignment program (European Bioinformatics Institute). Oligonucleotides representing each of the 18 highly conserved sequence blocks identified across the 16S genomic loci are synthesized and mixed in equimolar proportions.

The pool of primer extension probes is combined with the test DNA library (above) containing the forward adaptor and the HotStarTaq PCR mastermix (QIAGEN, USA) containing buffer, dNTPs, and a thermally-activated Taq DNA polymerase. This solution is placed in a thermal cycler, heated to 95° C. for 15 minutes to activate the polymerase and cooled to 70° C. for 5 minutes to allow the 16S primers to anneal to DNA inserts and extend into the forward adaptor site. Amplification primers that bind to the forward and reverse adaptor sites are added. Selection for fragments that contain both the forward (test library) and reverse (5' common region on 16S primers) adaptor, and the respective universal priming sites, is accomplished with PCR using a 3-step temperature routine (94° C. for 30 seconds, 60° C. for 30 seconds, 72° C. for 1 minute) for 25 cycles. PCR products are purified using AMPure XP beads and analyzed with a 2100 Bioanalyzer (Agilent Technologies).

Sequencing and Data Analysis

Single end sequencing reads of 100 nt length are obtained for both the control and enriched test libraries using a MiSeq System (Illumina). Raw sequencing data is processed using Illumina base calling software and mapped to a ribosomal RNA database. Sequences that do not align to bacterial rRNA are mapped to human and bacterial full genome reference sequences. Fold enrichment is determined by calculating the number of rRNA reads as a percentage of total mapped reads in the control and test samples.

Example 2

Characterization of Changes Over Time to the Human Oral Microbiome by Selective Enrichment of Bacterial 16S Ribosomal DNA Sequences Sample Nucleic Acid Microbial genomic DNA is isolated from human saliva using the OMNigene-DISCOVER sample collection kit (DNA Genotek) according to the manufacturer's instructions at 1 hour intervals for 16 hours following use of dental rinse. Extracted DNA is then fragmented via sonication to an average length of 400 by and purified using Agencourt AMPure XP beads (Beckman Coulter Genomics).

Generation of DNA Fragments with Ligated Forward Adapters

Components from the NuGEN Ovation Ultralow Library System (NuGEN Technologies) are used to generate 16 independent next generation sequencing libraries from 100 ng of the purified sample. Briefly, DNA is blunted and prepared for ligation under the standard end-repair reaction conditions described in the kit. Fragments are then ligated to the forward adapter only. As depicted in FIG. 2, ligation attaches the forward adapter to each end of each DNA fragment, leaving a single-strand nick on the opposite strand. Adapter fill-in will be performed, thus generating ligation products where complementary ends exist on each insert.

Ligation products of at least 100 by in length are purified by selective binding to Agencourt AMPure XP beads and taken forward into the enrichment process.

Primer Extension

Libraries containing ribosomal genes are generated by introducing the reverse adapter attached to the 5' end of oligonucleotides specific to conserved regions within these genes. There are two distinct steps: 1) annealing of the gene-specific primer; and 2) extension of that primer through the action of a DNA polymerase. The resulting product is a functional library containing the forward adapter on one end and the reverse adapter on the other end. The gene-specific primer extension step is performed with oligonucleotides containing a 3' gene-specific region and a 5' region that contains a portion of the Illumina reverse adapter sequence. Embedded in the reverse adapter sequence is a variable region of 8 bases that differentiates this adapter from the 16 other adapters used with the other samples. Thus, 16 gene-specific libraries have been generated; one from each sample. Each library has a common forward adapter. Each library also contains a common sequence on the opposite end but within that common sequence there is a unique 8 nucleotide region. Consensus 16S sequences making up the gene-specific segment are selected by comparing the ribosomal operons from 40 diverse bacterial species using the ClustalW multiple sequence alignment program (European Bioinformatics Institute). Oligonucleotides representing each of the 18 highly conserved sequence blocks identified across the 16S genomic loci are synthesized and mixed in equimolar proportions.

Individual samples with forward adapters ligated onto each strand are combined with the primer extension probes (described above) in 16 independent reactions. These are mixed with HotStarTaq PCR mastermix (QIAGEN, USA) containing buffer, dNTPs, and a thermally-activatable Taq DNA polymerase. This solution is placed in a thermal cycler, heated to 95° C. for 15 minutes to activate the polymerase and cooled to 70° C. for 5 minutes to allow the 16S primers to anneal to DNA inserts and extend into the forward adapter site.

Amplification

The 16 individual primer extension products (above) are pooled, amplification primers that are complementary to the 5' ends of the forward and reverse adapter sites but also contain portions complementary to flow cell oligonucleotide sequences are added. Selection for fragments that contain both the forward and reverse (5' common region on 16S primers) adapter, and the respective universal priming sites, is accomplished with PCR using a 3-step temperature routine (94° C. for 30 seconds, 60° C. for 30 seconds, 72° C. for 1 minute) for 25 cycles. PCR products are purified using AMPure XP beads and analyzed with a 2100 Bioanalyzer (Agilent Technologies).

Sequencing and Data Analysis

Single end sequencing reads of 100 nt length are obtained for both the control and enriched test libraries using a MiSeq System (Illumina). Raw sequencing data is processed using Illumina base calling software. Samples from the various time points are binned based on their unique 8 base code and mapped to a ribosomal RNA database. Sequences that do not align to bacterial rRNA are mapped to human and bacterial full genome reference sequences. Changes in microbial populations are assessed by comparing 16S read counts from the different organisms in the samples over time.

Example 3

Characterization of Transcriptional Activity of Individual Cells Within a Population Sample Nucleic Acid Individual cells are isolated from whole blood using a FACS cell sorter. The cells are suspended in 10 µl of Prelude Lysis solution (a component of NuGEN Technologies, One Direct system), resulting in lysis of the cell membrane while the nuclear membrane remains intact. Sixteen of the single cell suspensions are selected for expression profiling. Briefly, kit reagents are used as described by the manufacturer to generate first and second strand cDNA from the total RNA present in the lysate. Double stranded cDNA products are purified using Agencourt AMPure XP beads (Beckman Coulter Genomics).

Generation of Fragments with Ligated Forward Adapters

Components from the NuGEN Ovation Ultralow Library System (NuGEN Technologies) are used to generate next generation sequencing libraries from each of the purified sample. Briefly, DNA is blunted and prepared for ligation under the standard end-repair reaction conditions described in the kit. Fragments are then ligated to the forward adapter only. As depicted in FIG. 2, ligation attaches the forward adapter to each end of each DNA fragment, leaving a single-strand nick on the opposite strand. Adapter fill-in will be performed, thus generating ligation products where complementary ends exist on each insert.

Ligation products of at least 100 by in length are purified by selective binding to Agencourt AMPure XP beads and taken forward into library generation.

Primer Extension

Libraries are generated by introducing the reverse adapter attached to the 5' end of a random hexamer. There are two distinct steps: 1) annealing of the primer; and 2) extension of that primer through the action of a DNA polymerase. The resulting product is a functional library containing the forward adapter on one end and reverse adapter on the other end. The primer extension step is performed with oligonucleotides containing a 3' random region and a 5' region that contains a portion of the Illumina reverse adapter sequence. Embedded in the reverse adapter sequence is a variable region of 8 bases that differentiates this adapter from the 16 other adapters used with the other samples. Thus, 16 libraries have been generated; one from each sample. Each library has a common forward adapter. Each library also contains a common sequence on the opposite end but within that common sequence there is a unique 8 nucleotide region.

Individual samples with forward adapters ligated onto each strand are combined with the primer extension probes (described above) in 16 independent reactions. These are mixed with HotStarTaq PCR mastermix (QIAGEN, USA) containing buffer, dNTPs, and a thermally-activatable Taq DNA polymerase. This solution is placed in a thermal cycler, heated to 95° C. for 15 minutes to activate the polymerase and cooled to 70° C. for 5 minutes to allow the primers to anneal to DNA inserts and extend into the forward adapter site.

Amplification

Amplification primers that are complementary to the 5' ends of the forward and reverse adapter sites but also contain portions complementary to flow cell oligonucleotide sequences are added to the 16 individual primer extension products (above). Selection for fragments that contain both the forward and reverse adapter, and the respective universal priming sites, is accomplished with PCR using a 3-step temperature routine (94° C. for 30 seconds, 60° C. for 30 seconds, 72° C. for 1 minute) for 25 cycles. PCR products are purified using AMPure XP beads and analyzed with a 2100 Bioanalyzer (Agilent Technologies).

Sequencing and Data Analysis

Equal masses of each of the amplified libraries (above) are pooled and diluted to working concentrations according to manufacturer's recommendations. Single end sequencing reads of 100 nt length are obtained for libraries using a MiSeq System (Illumina). Raw sequencing data is processed using Illumina base calling software. Samples from the various time points are binned based on their unique 8 base code and mapped to a reference database. Based on the mapping characteristics, individual samples or a new pool of samples can be rerun on the sequencer to obtain greater read depth. Samples with poor gene coverage will be eliminated from the pool.

What is claimed is:

1. A method for enriching for a nucleic acid sequence of interest in a sample comprising nucleic acids, the method comprising:
   (a) fragmenting nucleic acids in the sample comprising the nucleic acids, thereby generating nucleic acid fragments, wherein the nucleic acid fragments comprise the nucleic acid sequence of interest;
   (b) ligating a first adaptor sequence to a 5' end of the nucleic acid fragments, thereby generating nucleic acid fragments ligated to the first adaptor sequence;
   (c) purifying the nucleic acid fragments ligated to the first adaptor sequence;
   (d) annealing one or more oligonucleotides in solution to the nucleic acid sequence of interest in the purified nucleic acid fragments ligated to the first adaptor sequence, wherein the one or more oligonucleotides in solution comprise a 3' portion with at least 10 bases that are complementary to the nucleic acid sequence of interest and a 5' tail, wherein the 5' tail comprises a second adaptor sequence non-complementary to the sequence of interest;
   (e) extending the one or more oligonucleotides annealed to the nucleic acid sequence of interest in the nucleic acid fragments ligated to the first adaptor sequence with a polymerase in a reaction mixture, wherein the reaction mixture does not comprise a primer that anneals to sequence complementary to the first adaptor sequence, thereby generating one or more oligonucleotide extension products comprising sequence complementary to the ligated first adaptor sequence at a first end, sequence complementary to the nucleic acid sequence of interest, and the second adaptor sequence at a second end;
   (f) amplifying the one or more oligonucleotide extension products using a first primer that anneals to the complement of the first adaptor sequence and a second primer that anneals to a complement of the second adaptor sequence to enrich for the nucleic acid sequence of interest, wherein products of the amplifying comprise a 3' end with sequence complementary to a sequence on a surface, thereby providing an enriched nucleic acid sequence of interest;
   (g) annealing a strand of the products of the amplifying to the sequence on the surface using the 3' end with sequence complementary to the sequence on the surface; and
   (h) sequencing the enriched nucleic acid sequence of interest on a massively parallel sequencing platform.

2. The method of claim 1, wherein the nucleic acid sequence of interest comprises genomic DNA, RNA, or cDNA.

3. The method of claim 1, wherein the first adaptor sequence and the second adaptor sequence are distinct from each other.

4. The method of claim 1, wherein the first adaptor sequence and/or the second adaptor sequence comprise barcode sequence.

5. The method of claim 1, wherein the polymerase is a DNA polymerase.

6. The method of claim 5, wherein the DNA polymerase is a DNA polymerase without 3'-exonuclease activity.

7. The method of claim 1, wherein the one or more oligonucleotides comprise more than one oligonucleotide, and wherein each of the more than one oligonucleotides comprises a 3' portion that is complementary to a different nucleic acid sequence of interest in the nucleic acid fragments and a 5' portion comprising the second adaptor sequence.

8. The method of claim 1, wherein the nucleic acid fragments are double-stranded.

9. The method of claim 8, further comprising denaturing the purified nucleic acid fragments ligated to the first adaptor sequence prior to step (d), thereby generating single-stranded nucleic acid fragments ligated to the first adaptor sequence.

10. The method of claim 1, wherein the first adaptor sequence comprises a restriction and/or cleavage site for a nucleic acid modifying enzyme.

11. The method of claim 1, wherein the 3' portion of the one or more oligonucleotides comprises a random sequence.

12. The method of claim 1, wherein the first adaptor sequence is in a first strand of a partial duplex adaptor.

13. The method of claim 12, wherein the first strand is a long strand of the partial duplex adaptor.

14. The method of claim 12, wherein the partial duplex adaptor comprises a second strand, wherein the second strand is a short strand.

15. The method of claim 14, wherein the short strand is ligated to a 3' end of the nucleic acid fragments.

16. The method of claim 1, wherein the first adaptor sequence is in a ligation strand of a first adaptor, wherein the first adaptor comprises the ligation strand and a non-ligation strand, wherein the ligation strand ligates to a 5' end of the nucleic acid fragments.

17. The method of claim 1, wherein the sequencing comprises bridge amplification.

18. The method of claim 1, wherein the sequencing comprises use of four labeled reversible terminators.

19. The method of claim 1, wherein the sequencing comprises semiconductor sequencing.

20. The method of claim 1, further comprising purifying the nucleic acid fragments prior to step (b).

21. The method of claim 1, further comprising purifying the products of the amplifying prior to step (g).

22. The method of claim 1, wherein the 3' portion of the one or more oligonucleotides that hybridizes to the nucleic acid sequence of interest is synthesized precisely according to antisense sequence of the nucleic acid sequence of interest.

23. A method for enriching for a nucleic acid sequence of interest from a library, wherein the library comprises nucleic acid inserts comprising the nucleic acid sequence of interest, wherein the nucleic acid inserts have a first adaptor sequence attached on a first end and a second adaptor sequence attached on a second end, the method comprising:
   (a) denaturing the nucleic acid inserts with the first adaptor sequence on the first end and the second adaptor sequence on the second end, thereby generating a library of single-stranded nucleic acid inserts with the first adaptor sequence on a first end and the second adaptor sequence on a second end;

(b) annealing one or more oligonucleotides in solution to the sequence of interest in the single-stranded nucleic acid inserts with the first adaptor sequence on the first end and the second adaptor sequence on the second end, wherein the one or more oligonucleotides in solution comprise a 3' portion with at least 10 bases designed to be complementary to the nucleic acid sequence of interest present in the nucleic acid inserts and a 5' tail, wherein the 5' tail comprises a third adaptor sequence, wherein the third adaptor sequence is distinct from the first adaptor sequence and the second adaptor sequence, and the 5' tail is non-complementary to the sequence of interest;

(c) extending the one or more oligonucleotides with a polymerase in a reaction mixture, wherein the reaction mixture does not comprise a primer that anneals to sequence complementary to the first adaptor sequence or the second adaptor sequence, thereby generating one or more oligonucleotide extension products comprising sequence complementary to the first adaptor sequence at a first end, sequence complementary to the nucleic acid sequence of interest, and the third adaptor sequence at a second end;

(d) amplifying the one or more oligonucleotide extension products using a first primer that anneals to the complement of the first adaptor sequence and a second primer that anneals to a complement of the third adaptor sequence to enrich for the nucleic acid sequence of interest, wherein products of the amplifying comprise a 3' end with sequence complementary to a sequence on a surface, thereby providing an enriched nucleic acid sequence of interest;

(e) purifying the products of the amplifying;

(f) annealing a strand of the purified products of the amplifying to the sequence on the surface using the 3' end with sequence complementary to the sequence on the surface; and (g) sequencing the enriched nucleic acid sequence of interest on a massively parallel sequencing platform.

24. The method of claim 23, wherein the nucleic acid sequence of interest comprises genomic DNA, RNA or cDNA.

25. The method of claim 23, wherein the third adaptor sequence is the same among the one or more oligonucleotides.

26. The method of claim 23, wherein the first adaptor sequence and the second adaptor sequence are distinct from each other.

27. The method of claim 23, wherein the first adaptor sequence and the complement of the second adaptor sequence are the same.

28. The method of claim 23, wherein the first adaptor sequence, the second adaptor sequence and/or the third adaptor sequence comprise barcode sequence.

29. The method of claim 23, wherein the 3' portion of each of the one or more oligonucleotides comprises a random sequence.

30. The method of claim 23, wherein the sequencing comprises bridge amplification.

31. The method of claim 23, wherein the sequencing comprises use of four labeled reversible terminators.

32. The method of claim 23, wherein the sequencing comprises semiconductor sequencing.

33. The method of claim 23, wherein neither the first adaptor sequence nor the second adaptor sequence comprises a 3' block.

34. The method of claim 23, further comprising ligating the first adaptor sequence to the first end and the second adaptor sequence to the second end of the nucleic acid inserts prior to step (a), thereby generating the library of nucleic acid inserts with the first adaptor sequence on the first end and the second adaptor sequence on the second end.

35. The method of claim 34, further comprising purifying the nucleic acid inserts with the first adaptor sequence on the first end and the second adaptor sequence on the second end after the ligating.

36. The method of claim 23, wherein the 3' portion of the one or more oligonucleotides that hybridizes to the nucleic acid sequence of interest is synthesized precisely according to antisense sequence of the nucleic acid sequence of interest.

37. The method of claim 23, wherein the polymerase is a DNA polymerase without 3'-exonuclease activity.

* * * * *